United States Patent
Nishino et al.

(10) Patent No.: US 8,080,802 B2
(45) Date of Patent: Dec. 20, 2011

(54) RADIATION DETECTING APPARATUS, RADIOGRAPHIC IMAGE CAPTURING SYSTEM, AND RADIOGRAPHIC IMAGE CAPTURING METHOD

(75) Inventors: Naoyuki Nishino, Minami-ashigara (JP); Keiji Tsubota, Minami-ashigara (JP); Yasunori Ohta, Yokohama (JP); Yutaka Yoshida, Fuchu (JP); Masato Hattori, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 211 days.

(21) Appl. No.: 12/654,565

(22) Filed: Dec. 23, 2009

(65) Prior Publication Data

US 2011/0042574 A1 Feb. 24, 2011

(30) Foreign Application Priority Data

Dec. 26, 2008 (JP) ................................ 2008-335179
Nov. 30, 2009 (JP) ................................ 2009-271493

(51) Int. Cl.
*H01L 27/146* (2006.01)
(52) U.S. Cl. ............................................. 250/370.08
(58) Field of Classification Search ........ 250/370.01–370.15; 378/98.8
See application file for complete search history.

(56) References Cited

U.S. PATENT DOCUMENTS

| | | | | |
|---|---|---|---|---|
| 5,844,961 A * | 12/1998 | McEvoy et al. | | 378/98.8 |
| 7,737,427 B2 * | 6/2010 | Kito et al. | | 250/580 |
| 7,822,180 B2 * | 10/2010 | Coombs | | 378/115 |
| 2008/0107234 A1 * | 5/2008 | Amitani | | 378/98.5 |
| 2009/0028295 A1 * | 1/2009 | Ohta et al. | | 378/98 |

FOREIGN PATENT DOCUMENTS

| | | |
|---|---|---|
| JP | 2000-105297 | 4/2000 |
| JP | 3494683 | 11/2003 |
| JP | 2008-170315 | 7/2008 |

* cited by examiner

*Primary Examiner* — Kiho Kim
(74) *Attorney, Agent, or Firm* — Jean C. Edwards, Esq.; Edwards Neils PLLC

(57) ABSTRACT

In a radiographic image capturing system, when a radiation detector is activated by a battery which is capable of being charged by a charging apparatus, charging of the battery by the charging apparatus is controlled based on whether image-capturing with respect to a subject is performed or not and/or whether delivery of the radiographic image information from the radiation detector is performed or not.

23 Claims, 17 Drawing Sheets

RADIATION DETECTING APPARATUS, RADIOGRAPHIC IMAGE CAPTURING SYSTEM, AND RADIOGRAPHIC IMAGE CAPTURING METHOD

CROSS-REFERENCE TO RELATED APPLICATION

This application is based upon and claims the benefit of priority from Patent Applications No. 2008-335179 filed on Dec. 26, 2008 and No. 2009-271493 filed on Nov. 30, 2009, in the Japan Patent Office, of which the contents are incorporated herein by reference.

BACKGROUND OF THE INVENTION

1. Field of the Invention

The present invention relates to a radiation detecting apparatus having a radiation detector for detecting radiation which has passed through a subject and converting the detected radiation into radiographic image information, a radiographic image capturing system having such a radiation detecting apparatus, and a radiographic image capturing method.

2. Description of the Related Art

In the medical field, there have widely been used radiographic image capturing apparatus, which apply radiation to a subject and guide the radiation that has passed through the subject to a radiation conversion panel, which captures a radiographic image from the radiation. Known forms of the radiation conversion panel include a conventional radiation film for recording a radiographic image by way of exposure, and a stimulable phosphor panel for storing radiation energy representing a radiographic image in a phosphor and reproducing the radiographic image as stimulated light by applying stimulating light to the phosphor. The radiation film with the recorded radiographic image is supplied to a developing device to develop the radiographic image, or the stimulable phosphor panel is supplied to a reading device to read the radiographic image as a visible image.

In the operating room or the like, it is necessary to read and display a recorded radiographic image immediately from a radiation conversion panel after the radiographic image has been captured for the purpose of quickly and appropriately treating the patient. Patients such as infants, children, aged people, or those who cannot stand themselves for a long time due to illness or injuries also need to be imaged quickly. As a radiation conversion panel which meets such a requirement, there has been developed a direct-conversion-type radiation detector for converting radiation directly into electric signals or an indirect-conversion-type radiation detector for converting radiation into visible light with a scintillator and then converting the visible light into electric signals with a solid-state detector to read a detected radiographic image.

Japanese Laid-Open Patent Publication No. 2008-170315 discloses that a battery for activating a radiation detector of a radiation detecting apparatus (electronic cassette) is contactlessly charged.

However, Japanese Laid-Open Patent Publication No. 2008-170315 does not propose a relationship between the image-capturing timing with respect to a subject and the timing of charging the battery by an external charging unit and/or between the timing of delivery of radiographic image information from the radiation detector and the timing of charging the battery by an external charging unit. Accordingly, if the battery is charged by the charging unit during image-capturing of the subject or during delivery of the radiographic image information, noise due to the charging may adversely affect the radiographic image information, thereby producing the radiographic image information that is not suitable for diagnosis based on interpretation of radiogram.

SUMMARY OF THE INVENTION

It is an object of the present invention to provide a radiation detecting apparatus, a radiographic image capturing system, and a radiographic image capturing method which are capable of obtaining radiographic image information of high quality by preventing noise due to charging of a battery from adversely affecting the radiographic image information, and which make it possible to charge the battery efficiently without adverse effects.

A radiation detecting apparatus according to the present invention comprises a radiation detector for detecting radiation applied from an external image capturing apparatus and transmitted through a subject and converting the detected radiation into radiographic image information, a battery for activating the radiation detector, a determining unit for determining whether image-capturing with respect to the subject is performed or not, and/or whether delivery of the radiographic image information from the radiation detector is performed or not, and a charging controller for controlling charging of the battery by an external charging apparatus based on a determination result by the determining unit.

Also, a radiographic image capturing system according to the present invention comprises an image capturing apparatus for applying radiation to a subject, a radiation detecting apparatus including a radiation detector for detecting the radiation transmitted through the subject and converting the detected radiation into radiographic image information, and a battery for activating the radiation detector, a determining unit for determining whether image-capturing with respect to the subject is performed or not, and/or whether delivery of the radiographic image information from the radiation detector is performed or not, a charging apparatus which is capable of charging the battery, a controller for controlling the image capturing apparatus, the radiation detecting apparatus, and the charging apparatus, and a charging controller for controlling charging of the battery by the charging apparatus based on a determination result by the determining unit.

According to the present invention, there is further provided a method of capturing a radiographic image by applying radiation to a subject by an image capturing apparatus, detecting the radiation with a radiation detector of a radiation detecting apparatus, and converting the detected radiation into radiographic image information with the radiation detector, the method comprising the step of, when the radiation detector is activated by a battery which is capable of being charged by the charging apparatus, controlling charging of the battery by a charging apparatus based on whether image-capturing with respect to the subject is performed or not, and/or whether delivery of the radiographic image information from the radiation detector is performed or not.

As described above, according to the present invention, charging of the battery by the power feeder is controlled based on whether image-capturing with respect to the subject have been performed or not, and/or whether delivery of the radiographic image information from the radiation detector has been performed or not. Thus, noise due to charging of the battery 44 is prevented from adversely affecting the radiographic image information, and then it is possible to obtain radiographic image information of high quality. Additionally, it is possible to charge the battery efficiently without adverse influences on the radiographic image information.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
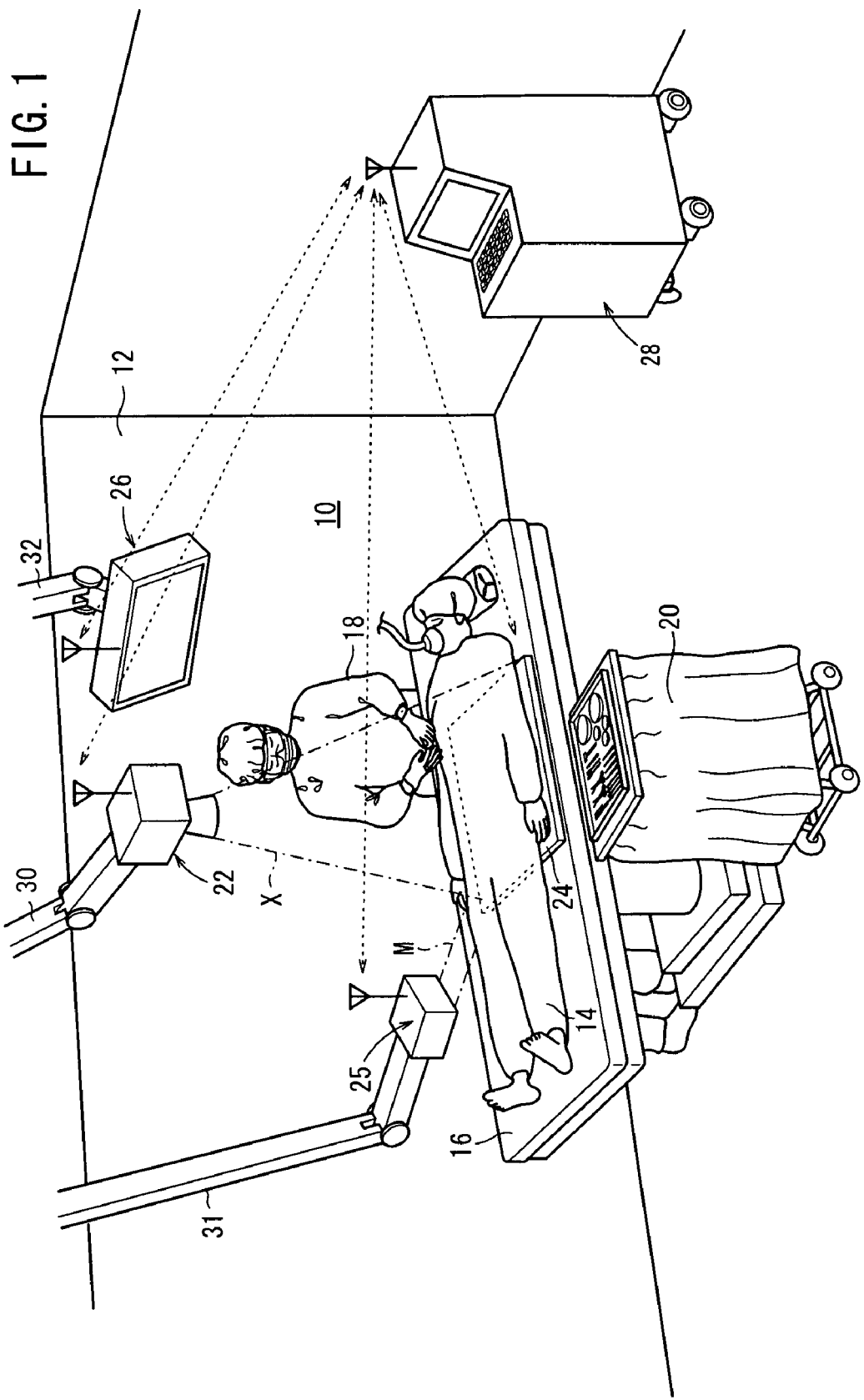
FIG. 1 is a perspective view of an operating room incorporating a radiographic image capturing system according to a first embodiment of the present invention.

Like or corresponding parts are denoted by like or corresponding reference characters throughout views.

Radiographic image capturing systems and radiographic image capturing methods according to preferred embodiments of the present invention, in reference to radiation detecting apparatus used in the radiographic image capturing systems, will be described in detail below with reference to the accompanying drawings.

As shown in FIG. 1, an operating room 12 houses therein a radiographic image capturing system 10 (hereinafter also referred to as "image capturing system 10") according to a first embodiment of the present invention. The operating room 12 houses, in addition to the radiographic image capturing system 10, a surgical table or bed 16 for a patient 14 to lie thereon, and an instrument table 20 disposed on one side of the surgical table 16 for placing thereon various tools and instruments to be used by a surgeon 18 for operating the patient 14. The surgical table 16 is surrounded by various apparatus required for surgical operations, including an anesthesia apparatus, an aspirator, an electrocardiograph, a blood pressure monitor, etc (not shown).

The image capturing system 10 includes an image capturing apparatus (radiation applying apparatus) 22 for irradiating the patient 14 as a subject with radiation X at a dose according to image capturing conditions, an electronic cassette (radiation detecting apparatus) 24 housing therein a radiation detector 40 (see FIG. 2) for detecting the radiation X that has passed through the patient 14, a power feeder (charging apparatus, contactless power feeder, wireless power feeder) 25 for supplying electric power wirelessly (contactlessly) to a battery 44 (see FIG. 2) housed in the electronic cassette 24, a display device 26 for displaying a radiographic image based on the radiation X that has been detected by the radiation detector 40, and a console (controller) 28 for generally controlling the image capturing system 10. The image capturing apparatus 22, the electronic cassette 24, the power feeder 25, the display device 26, and the console 28 send and receive signals by way of wireless communications using UWB (Ultra Wide Band), WiFi (Wireless Fidelity) such as IEEE 802.11.a/g/n, or millimeter waves.

Since the power feeder 25 and the electronic cassette 24 are out of contact with each other, a contactless power feeding technique for feeding power contactlessly (wirelessly) is adopted as a technique for feeding power to (the battery 44 of) the electronic cassette 24 by the power feeder 25, as described above.

Specifically, the contactless power feeding technique includes (1) a microwave power feeding technique in which the power feeder 25 feeds power to the electronic cassette 24 using an electromagnetic wave in the microwave band, (2) an electromagnetic induction power feeding technique in which the power feeder 25 feeds power to the electronic cassette 24 by electromagnetic induction with the coil of the power feeder 25 being in proximity to the coil of the electronic cassette 24, and (3) a resonance power feeding technique in which the power feeder 25 feeds power to the electronic cassette 24 using electromagnetic resonance between the power feeder 25 and the electronic cassette 24.

Also, the above resonance power feeding technique (3) includes a magnetic resonance power feeding technique. In the magnetic resonance power feeding technique, the coils of the power feeder 25 and the electronic cassette 24 are adjusted to have substantially the same resonant frequency, and the coil of the power feeder 25 on the sending side generates electromagnetic field caused by high-frequency electric power in a given space of the operating room 12, while the coil of the electronic cassette 24 on the receiving side is placed in the generated electromagnetic field, whereby the coil of the electronic cassette 24 can receive the high-frequency electric power.

Incidentally, the contactless power feeding technique for feeding power to the electronic cassette 24 by the power feeder 25 (microwave type, electromagnetic induction type, resonance type, magnetic resonance type) can adopt a conventional contactless power feeding technique.

Hereinafter, if not otherwise specified, the power feeder 25 feeds power to the battery 44 of the electronic cassette 24 using a magnetic resonance power feeding technique.

The image capturing apparatus 22 is coupled to a universal arm 30 extending from the ceiling of the operating room 12 so as to be movable to a desired position for capturing an image of a desired area of the patient 14 and also to be retractable to a position out of the way while the surgeon 18 is performing a surgical operation on the patient 14. Similarly, the power feeder 25 is coupled to a universal arm 31 so as to be movable to a desired position depending on the location of the electronic cassette 24. The display device 26 is coupled to a universal arm 32 so as to be movable to a position where the surgeon 18 can easily confirm a captured radiographic image displayed on the display device 26. The universal arms 30, 31, 32 may alternatively be mounted on a wall, a floor, or a movable cart. The power feeder 25 and the display device 26 may alternatively be fixed to the ceiling, a wall, or a floor rather than being supported on the universal arms. The power feeder 25 should preferably be positioned horizontally laterally of the radiation detecting apparatus (the electronic cassette 24) (see FIGS. 1 and 14) or on the bottom side of the radiation detecting apparatus (see FIG. 15) so that a magnetic field M (electromagnetic field due to high-frequency electric power) applied from the power feeder 25 to the radiation detecting apparatus will be kept out of direct interference with the patient 14.

Figure 2:
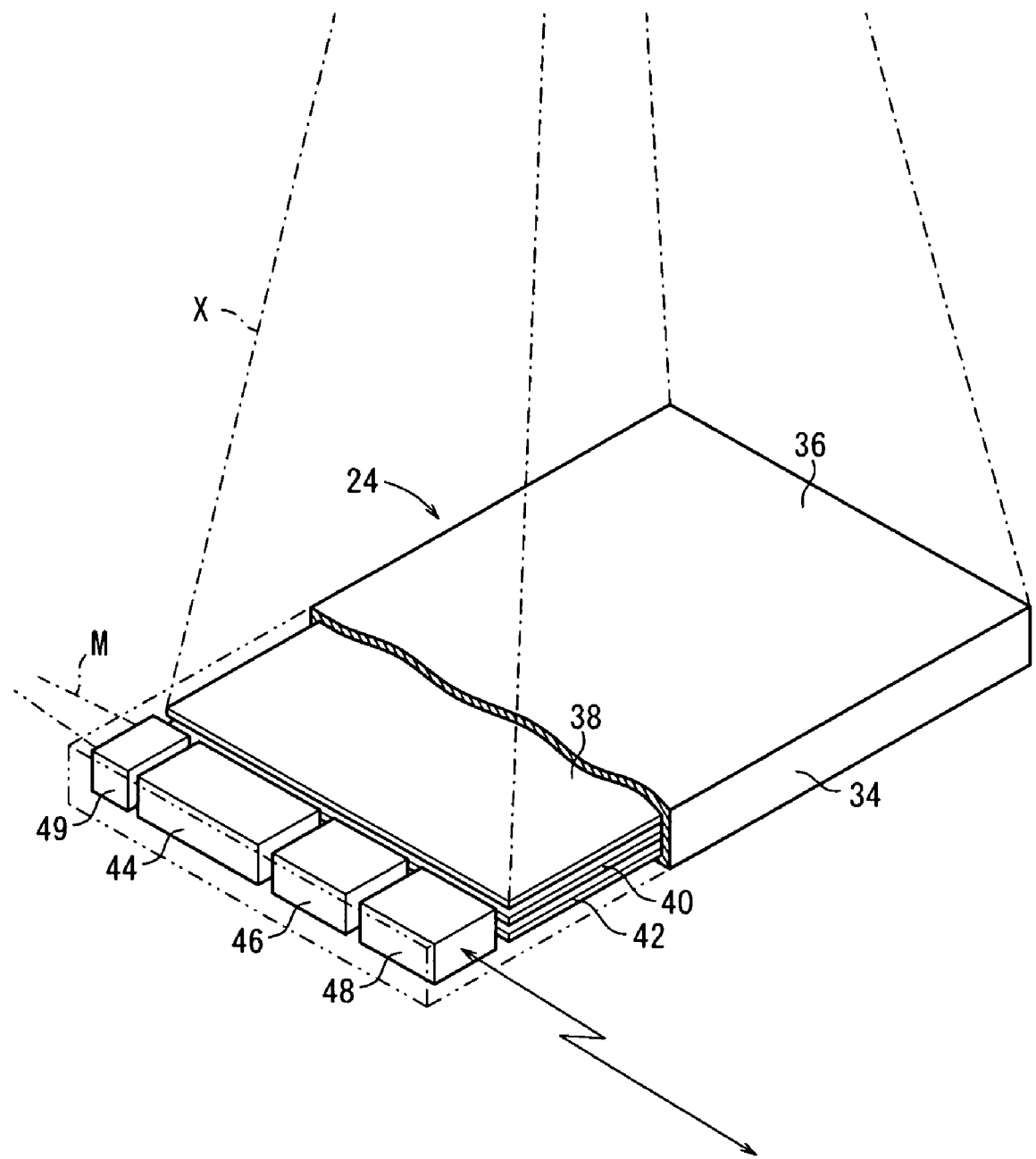
FIG. 2 is a perspective view, partly cut away, showing internal structural details of an electronic cassette used in the radiographic image capturing system shown in FIG. 1.

FIG. 2 shows in perspective internal structural details of the electronic cassette 24. As shown in FIG. 2, the electronic cassette 24 has a box-shaped casing 34 made of a material permeable to the radiation X. The casing 34 houses therein a grid 38 for removing scattered rays of the radiation X from the patient 14, a radiation detector (radiation conversion panel) 40 for detecting the radiation X that has passed through the patient 14, and a lead plate 42 for absorbing back scattered rays of the radiation X, which are successively arranged in the order named from a surface 36 of the casing 34 which is irradiated with the radiation X. The irradiated surface 36 of the casing 34 may be constructed as the grid 38.

The casing 34 also houses therein a battery 44 serving as a power supply of the electronic cassette 24, a cassette controller 46 for energizing the radiation detector 40 with electric power supplied from the battery 44, and a transceiver 48 for sending and receiving signals including the information of the radiation X (radiographic image information) detected by the radiation detector 40, to and from the console 28 by wireless communications. A shield plate of lead or the like should preferably be placed over the side surfaces of the battery 44, the cassette controller 46, and the transceiver 48 under the irradiated surface 36 of the casing 34 to protect the battery 44, the cassette controller 46, and the transceiver 48 against damage which would otherwise be caused if irradiated with the radiation X. The casing 34 also houses therein a wireless power receiver (contactless power receiver) 49 for receiving the magnetic field (magnetic fluxes) M converted from electric energy (high-frequency electric power) and applied contactlessly (wirelessly) by the power feeder 25, and converting the magnetic field M back into electric energy.

Figure 3:
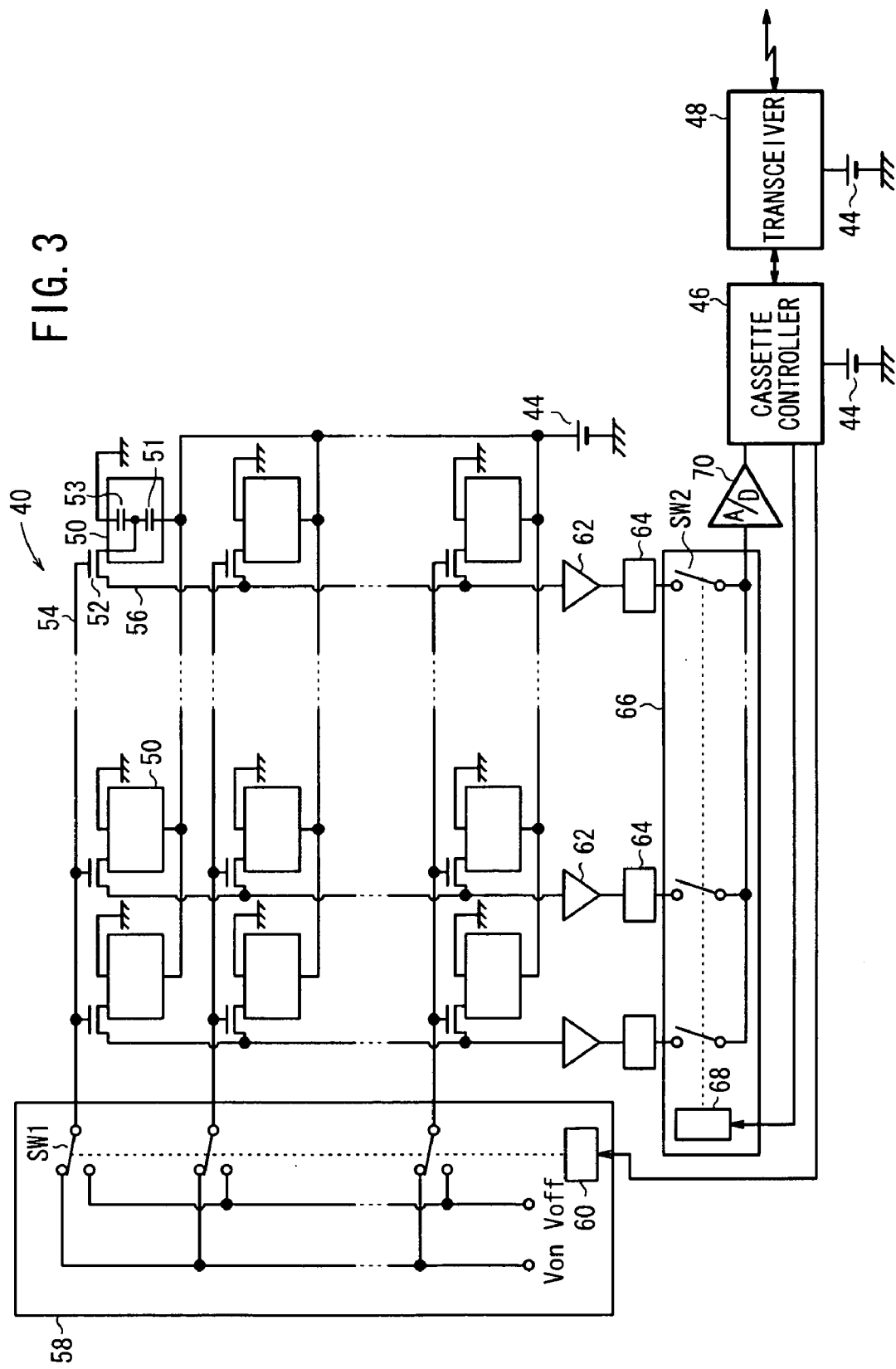
FIG. 3 is a block diagram of a circuit arrangement of a radiation detector in the electronic cassette shown in FIG. 2.

FIG. 3 shows in block form a circuit arrangement of the radiation detector 40. As shown in FIG. 3, the radiation detector 40 comprises a direct-conversion-type radiation detector. In this case, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed over the array of TFTs 52, and an array of storage capacitors (storage devices) 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used within a certain temperature range. Therefore, some means for cooling the radiation detector 40 should preferably be provided in the electronic cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiographic image signal generated by the multiplexer 66 based on the electric charges from the sample and hold circuits 64 is converted by the A/D converter 70 into a digital image signal representing radiographic image information, which is supplied to the cassette controller 46.

The TFTs 52 which function as switching devices may be combined with another image capturing device such as a CMOS (Complementary Metal-Oxide Semiconductor) image sensor or the like. Alternatively, the TFTs 52 may be replaced with a CCD (Charge-Coupled Device) image sensor for shifting and transferring electric charges with shift pulses which correspond to gate signals in the TFTs.

Figure 4:
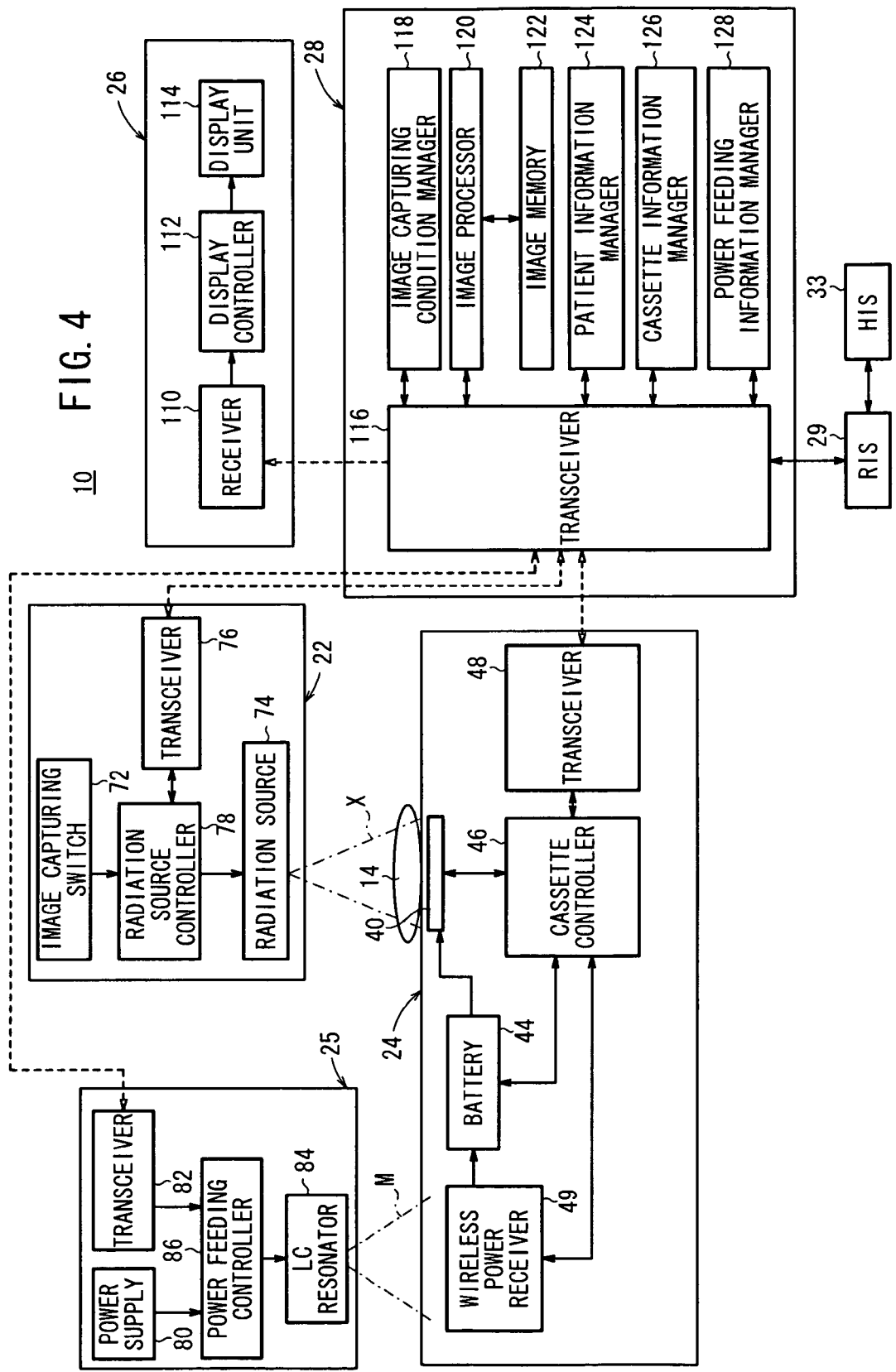
FIG. 4 is a block diagram of the radiographic image capturing system shown in FIG. 1.

FIG. 4 shows in block form the image capturing system 10 which comprises the image capturing apparatus 22, the electronic cassette 24, the power feeder 25, the display device 26, and the console 28.

The console 28 is connected to a radiology information system (RIS, information management system) 29 which stores and generally manages radiographic image information handled by the radiological department of the hospital and other information, e.g., ordering information representative of the number of times that the patient 14 is to be imaged (the number of radiographic images thereof to be captured, the number of times that the patient 14 is to be exposed to the radiation X). Also, the RIS 29 is connected to a hospital information system (HIS) 33 which generally manages medical information in the hospital. Alternatively, the console 28 may be connected to a consolidated system which combines the functions of the HIS 33 and the RIS 29.

The image capturing apparatus 22 comprises an image capturing switch 72, a radiation source 74, a transceiver 76 (signal transmitting/receiving unit), and a radiation source controller 78. The transceiver 76 receives image capturing conditions from the console 28 by way of wireless communications and transmits an image capturing completion signal, an image capturing start signal, etc. to the console 28 by way of wireless communications. The radiation source controller 78 controls the radiation source 74 based on an image capturing start signal (image capturing request signal) supplied from the image capturing switch 72 and image capturing conditions supplied from the console 28. The radiation source 74 outputs the radiation X under the control of the radiation source controller 78.

The power feeder 25 comprises a power supply 80 connected to an external power supply or the like, not shown, a transceiver (signal transmitting/receiving unit) 82 for receiving a power feeding start signal (power feeding start signal, charging permission signal), etc. from the console 28 by way of wireless communications and sending ID information (ID data), etc. of the power feeder 25 to the console 28 by way of wireless communications, an LC resonator (feeding unit) 84 for converting electric energy from the power supply 80 into the magnetic field M and applying the magnetic field M, or in other words, contactlessly (wirelessly) supplying electric energy, to the electronic cassette 24, and a power feeding controller 86 for energizing the LC resonator 84 based on the power feeding start signal supplied from the console 28.

Figure 5:
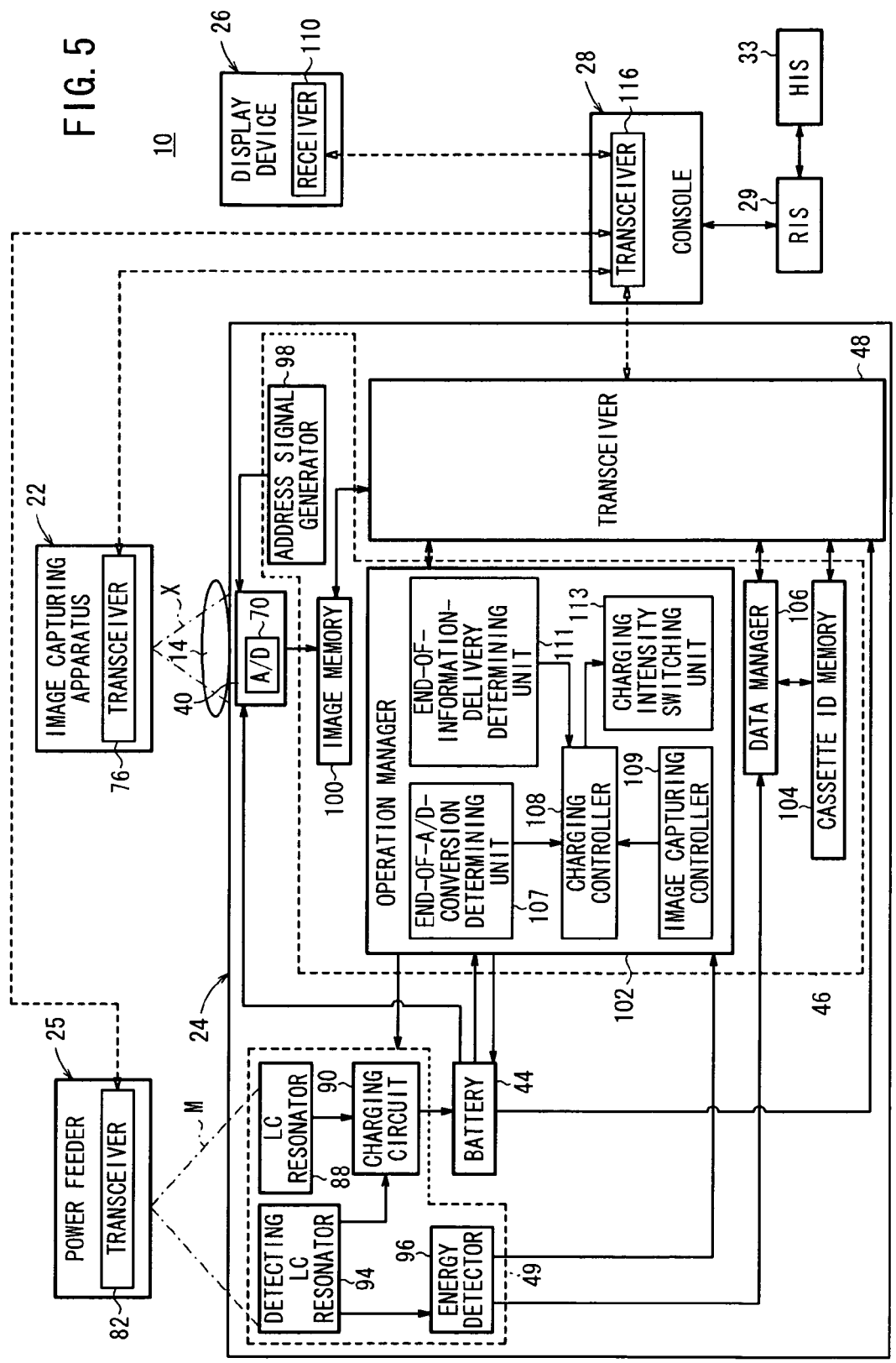
FIG. 5 is a block diagram of the radiographic image capturing system, showing structural details of the electronic cassette shown in FIG. 4.

FIG. 5 shows in block form the image capturing system 10, showing structural details of the electronic cassette 24 as the radiation detecting apparatus according to the present embodiment.

As shown in FIGS. 4 and 5, the electronic cassette 24 includes the radiation detector 40, the battery 44, the wireless power receiver 49, the cassette controller 46, and the transceiver (signal transmitting/receiving unit, wireless transceiver) 48.

The battery 44 comprises a chargeable secondary battery such as a lithium ion battery or the like, and serves as a power supply for supplying electric power to various parts of the electronic cassette 24, which include the radiation detector 40, the cassette controller 46, and the transceiver 48. The battery 44 may alternatively comprise an electric storage device such as an electric double layer capacitor or any of other devices insofar as it can be charged and serve as a power supply for the electronic cassette 24.

The wireless power receiver 49 has a function to receive the electric power contactlessly (wirelessly) supplied from the power feeder 25 and supply the received electric power to the battery 44, i.e., charge the battery 44 with the received electric power. The wireless power receiver 49 has an LC resonator 88 for receiving the magnetic field M applied from the LC resonator 84 of the power feeder 25 into electric energy (high-frequency power), and a charging circuit 90 for converting the electric energy from the LC resonator 88 into desired electric power and supplying the electric power to the battery 44. Specifically, the LC resonator 88 comprises an LC resonant circuit having a coil and a capacitor, and the charging circuit 90 rectifies the electric current generated by the LC resonator 88 into a constant electric current, and charges the battery 44 with the constant electric current.

The wireless power receiver 49 also has a detecting LC resonator 94 disposed parallel to the LC resonator 88 and smaller in size than the LC resonator 88, and an energy detector 96 for detecting electric energy converted from the magnetic field M by the detecting LC resonator 94. The detecting LC resonator 94 also comprises an LC resonant circuit having a coil and a capacitor, as with the LC resonator 88. When the energy detector 96 detects the electric energy converted from the magnetic field M by the detecting LC resonator 94, the energy detector 96 detects that the electronic cassette 24 is positioned within a feeding area of the power feeder 25, and sends a feeding area detection signal to the cassette controller 46.

Each of the LC resonators 84, 88, 94 has an LC resonance circuit comprising a coil and a capacitor. The power feeder 25 can contactlessly (wirelessly) supply electric power to the electronic cassette 24 according to the known power transmission technology which utilizes the resonance of the magnetic field M (magnetic resonance) from the LC resonator 84 to the LC resonator 88.

As shown in FIG. 5, the cassette controller 46 comprises an address signal generator 98, an image memory 100, an operation manager 102, a cassette ID memory 104, and a data manager 106. The address signal generator 98 supplies address signals to the address decoder 60 of the line scanning driver 58 of the radiation detector 40 and the address decoder 68 of the multiplexer 66 of the radiation detector 40. The image memory 100 stores radiographic image information detected by the radiation detector 40. Specifically, the image memory 100 stores radiographic image information generated by the radiation detector 40 when the radiation X is applied to the radiation detector 40 and converted into electric charges, and the electric charges are stored and then read and converted into digital signals.

The operation manager 102 controls operation of the wireless power receiver 49 and the battery 44, and also controls overall operation of the electronic cassette 24. The operation manager 102 comprises an end-of-A/D-conversion determining unit (determining unit) 107, an end-of-information-delivery determining unit (determining unit) 111, a charging controller 108, an image capturing controller 109, and a charging-intensity switching unit 113.

The end-of-A/D-conversion determining unit 107 determines whether the A/D conversion of radiographic image information by the A/D converter 70 is ended or not. The end-of-information-delivery determining unit 111 determines whether any one of: transfer of digital radiographic image information from the A/D converter 70 to the image memory 100, storage of the digital radiographic image information into the image memory 100, and transmission (output) of the digital radiographic image information from the image memory 100 to the console 28 through the transceivers 48, 116 is ended or not. The image capturing controller 109 generates a control signal (image capturing permission signal) for permitting the image capturing apparatus 22 to capture a radiographic image (to apply radiation X) and a control signal (image capturing inhibition signal) for inhibiting the image capturing apparatus 22 from capturing a radiographic image.

When the end-of-A/D-conversion determining unit 107 judges that the A/D conversion is ended, the charging controller 108 determines that the battery 44 should be charged at a first charging intensity, and generates a signal (power feeding permission signal, power feeding start signal, charging permission signal) for permitting the power feeder 25 to supply (charge) the electronic cassette 24 with electricity. Also, when the end-of-information-delivery determining unit 111 judges that any one of transfer of digital radiographic image information from the A/D converter 70 to the image memory 100, storage of the digital radiographic image information into the image memory 100, and transmission (output) of the digital radiographic image information from the image memory 100 to the console 28 through the transceivers 48, 116 is ended, the charging controller 108 determines that the battery 44 should be charged at a second charging intensity which is higher than the first charging intensity.

Further, when the image capturing controller 109 generates the image capturing permission signal, the charging controller 108 generates the signal (power feeding inhibition signal, charging inhibition signal) for inhibiting the power feeder 25 from supplying (charging) the electronic cassette 24 with electric power. Still further, when the image capturing controller 109 generates the image capturing inhibition signal, the charging controller 108 generates the signal (power feeding permission signal, charging permission signal) for permitting the power feeder 25 to supply (charge) the electronic cassette 24 with electric power.

As described above, the charging controller 108 generates the power feeding inhibition signal and the power feeding permission signal in response to a judgment result by the end-of-A/D-conversion determining unit 107, a judgment result by the end-of-information-delivery determining unit 111, and a signal from the image capturing controller 109. Thus, the charging controller 108 may serve as a plurality of controllers (signal generators) which respond respectively to the power feeding inhibition signal and the power feeding permission signal.

When the charging controller 108 determines charging of the battery 44 at the first charging intensity, the charging-intensity switching unit 113 generates a control signal (first charging control signal) for controlling the power feeder 25 to charge the battery 44 at the first charging intensity. Also, when the charging controller 108 determines charging of the battery 44 at the second charging intensity, the charging intensity switching unit 113 generates a control signal (second charging control signal) for controlling the power feeder 25 to charge the battery 44 at the second charging intensity.

The charging intensity refers to a level of supply energy in association with charging of the battery 44 by the power feeder 25, for example, the amount of electric energy which is supplied to the LC resonator 84, the magnitude of voltage which is applied to the LC resonator 84, the amount of electric current which flows through the LC resonator 84, the magnitude of magnetic field M, the amount of electric energy which is reconverted by the LC resonator 88 or the detecting LC resonator 94, the magnitude of voltage which is generated in the LC resonator 88 or the detecting LC resonator 94, or the amount of electric current which flows out of the LC resonator 88 or the detecting LC resonator 94. The first charging intensity refers to a charging intensity of a relatively low level, for example, such a low level that noise due to charging of the battery 44 does not adversely affect the digital radiographic image information which has been converted by the A/D converter 70. The second charging intensity refers to a charging intensity of a relatively high level, for example, a level for normal charging of the battery 44. If noise depends on frequency, higher frequency provides more noise that adversely affects the radiographic image information. Thus, it is desirable to set the first charging intensity at a low-frequency charging intensity and set the second charging intensity at a high-frequency charging intensity.

The feeding inhibition signal and the feeding permission signal which are generated by the charging controller 108, the image capturing permission signal and the image capturing inhibition signal which are generated by the image capturing controller 109, the first and second charging control signals which are generated by the charging intensity switching unit 113 are transmitted from the transceiver 48 to the console 28. When the console 28 receives these signals, the console 28 performs a control process for inhibiting (stopping) the contactless power feeding (wireless power feeding) from the power feeder 25, a control process for starting (resuming) the contactless power feeding (wireless power feeding) from the power feeder 25, and a control process for controlling the charging intensity, and also performs a control process for permitting (starting) the image capturing by the image capturing apparatus 22 and a control process for inhibiting (stopping) the image capturing by the image capturing apparatus 22. Alternatively, the electronic cassette 24 may directly transmit the feeding inhibition (permission) signal, the image capturing permission (inhibition) signal and the first and second charging control signals to the power feeder 25, not through the console 28, and the power feeding controller 86 and the radiation source controller 78 may perform the control process for inhibiting (starting) the contactless power feeding (wireless power feeding), the control process for starting (inhibiting) the image capturing, and the control process for controlling the charging intensity.

The cassette ID memory 104 stores cassette ID information for identifying the electronic cassette 24. The data manager 106 manages ID information (ID data) for identifying the power feeder 25 which feeds the electronic cassette 24 and a feeding area detection signal from the energy detector 96. Also, the data manager 106 generates a wireless feeding enable signal indicating that the power feeder 25 can feed electric power, based on the feeding area detection signal.

The transceiver 48 receives a transmission request signal from the console 28 and the ID information of the power feeder 25 by way of wireless communications, and transmits the radiographic image information, the cassette ID information, a wireless feeding enable signal, the feeding inhibition signal, the feeding permission signal, the image capturing permission signal, the image capturing inhibition signal, the first and second charging control signals, etc. to the console 28.

As shown in FIG. 4, the display device 26 comprises a receiver 110 for receiving the radiographic image information from the console 28, a display controller 112 for processing the received radiographic image information, and a display unit 114 for displaying the radiographic image information processed by the display controller 112.

The console 28 comprises a transceiver (signal transmitting/receiving unit) 116, an image capturing condition manager 118, an image processor 120, an image memory 122, a patient information manager 124, a cassette information manager 126, and a power feeding information manager 128. The console 28 may be located outside of the operating room 12 insofar as it can reliably transmit and receive signals to and from the image capturing apparatus 22, the electronic cassette 24, the power feeder 25, and the display device 26.

The transceiver 116 of the console 28 transmits and receives necessary information including radiographic image information, the feeding inhibition (permission) signal, the image capturing permission (inhibition) signal, and the first and second charging control signals to and from the image capturing apparatus 22, the electronic cassette 24, the power feeder 25, and the display device 26 by way of wireless communications. The image capturing condition manager 118 manages image capturing conditions required for the image capturing apparatus 22 to capture radiographic images, and also performs the control process for starting the image capturing by the image capturing apparatus 22 and the control process for inhibiting the image capturing by the image capturing apparatus 22 based on the image capturing permission signal and the image capturing inhibition signal from the image capturing controller 109. The image processor 120 processes radiographic image information transmitted from the electronic cassette 24. The image memory 122 stores the radiographic image information processed by the image processor 120. The patient information manager 124 manages patient information of the patient 14 whose images are to be captured. The cassette information manager 126 manages the wireless feeding enable signal and the cassette information including the cassette ID information transmitted from the electronic cassette 24. The power feeding information manager 128 manages the operation control of the power feeder 25 and ID information sent from the power feeder 25, and also performs the control process for inhibiting the power feeding by the power feeder 25 and the control process for starting (resuming) the power feeding by the power feeder 25 based on the feeding inhibition signal and the feeding permission signal from the charging controller 108. Also, the power feeding information manager 128 performs a switching control for switching the charging intensity at which the power feeder 25 charges the electronic cassette 24 (switching between the first and second charging intensities), based on the first and second charging control signals from the charging intensity switching unit 113.

The image capturing conditions refer to conditions for determining a tube voltage, a tube current, an irradiation time, etc. required to apply radiation X at an appropriate dose to an area to be imaged of the patient 14. The image capturing conditions may include an area to be imaged of the patient 14, an image capturing method, etc., for example. The image capturing conditions may also include conditions representing the number of times that a radiographic image is to be captured, as ordering information from the RIS 29, for example. The patient information refers to information for identifying the patient 14, such as the name, gender, patient ID number, etc. of the patient 14. Ordering information for instructing the image capturing system 10 to capture a radiation image, including the image capturing conditions and the patient information, can be set directly on the console 28 or can be supplied from an external source to the console 28 via the RIS 29. The cassette information includes the wireless feeding enable signal from the data manager 106 in addition to the cassette ID information for identifying the electronic cassette 24.

The image capturing system 10 according to the first embodiment is basically constructed as described above, and operation (radiographic image capturing method) of the image capturing system 10 will be described below with reference to a flowchart shown in FIG. 6.

The operation of the image capturing system 10 will be described below in the case where the number of images to be captured is one and the end-of-information-delivery determining unit 111 determines whether transfer of digital radiographic image information from the A/D converter 70 to the image memory 100 is ended or not.

The image capturing system 10 is installed in the operating room 12 and used when radiographic images of the patient 14 are required by the surgeon 18 who is performing a surgical operation on the patient 14. Before radiographic images of the patient 14 are captured, patient information of the patient 14 to be imaged and the number of radiographic images to be captured are registered in the patient information manager 124 of the console 28. If an area to be imaged of the patient 14 and an image capturing method have already been known, they are registered beforehand as image capturing conditions in the image capturing condition manager 118. These information and conditions can be registered by being acquired from the RIS 29. After the above preparatory process is finished, the surgeon 18 performs a surgical operation on the patient 14.

Figure 6:
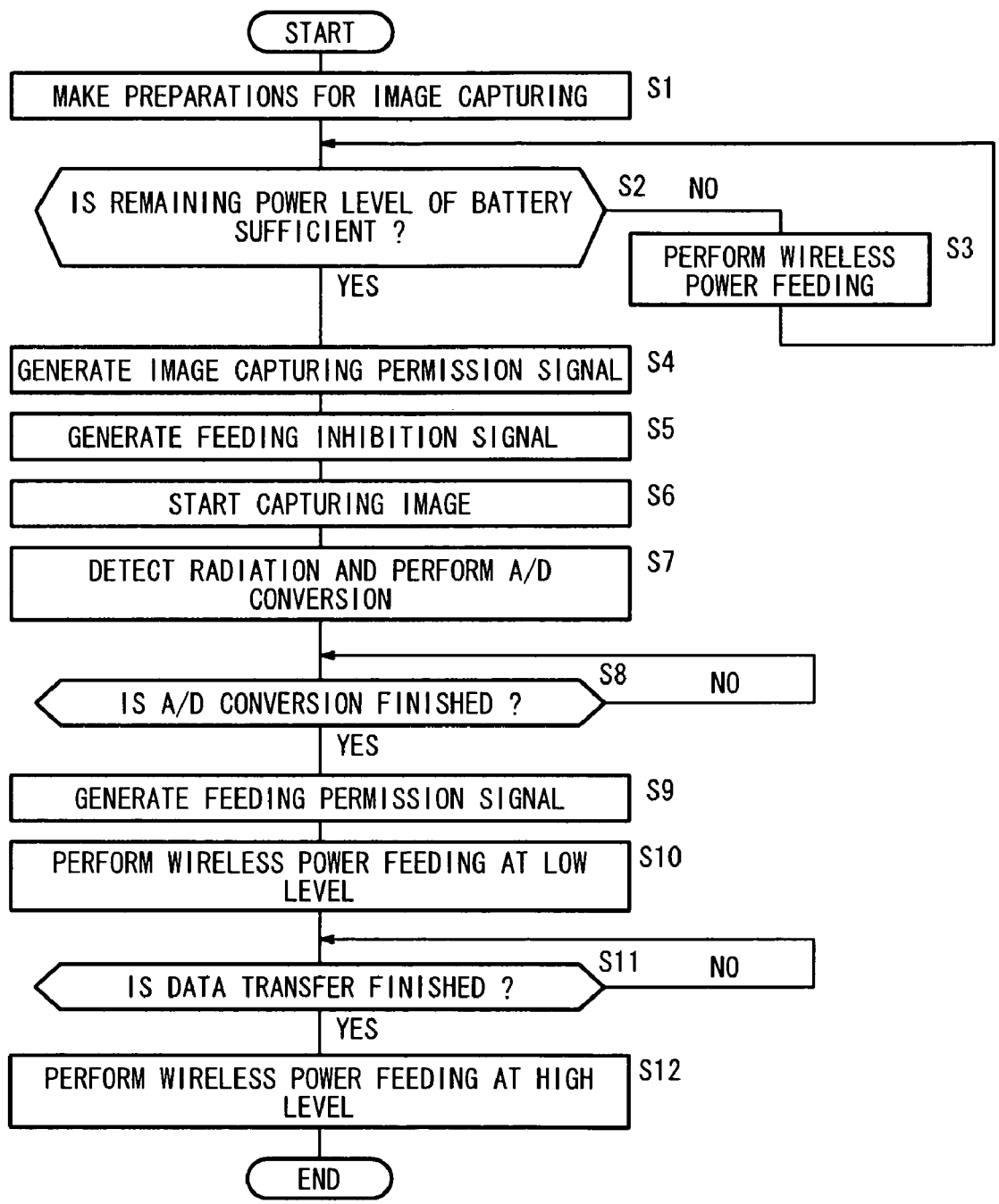
FIG. 6 is a flowchart of an image capturing sequence of the radiographic image capturing system shown in FIG. 4.

In step S1 shown in FIG. 6, for capturing radiographic images of the patient 14 during the surgical operation, the surgeon 18 or a radiological technician working on the image capturing system 10 places the electronic cassette 24 in a desired position between the patient 14 and the surgical table 16 with the irradiated surface 36 facing the image capturing apparatus 22.

At the same time that the console 28 starts to operate or when the surgeon 18 or the radiological technician turns on an operation start switch, not shown, the power feeder 25 is energized under given operating conditions (a low output operation mode). The electronic cassette 24 is now detected as being placed within the feeding area of the power feeder 25 by the detecting LC resonator 94 and the energy detector 96 of the wireless power receiver 49. Specifically, the energy detector 96 functions as a power feeding enable/disable detector for detecting whether the electronic cassette 24 is placed within the feeding area of the power feeder 25 or not. At this time, the power feeding controller 86 of the power feeder 25 operates in the low output operation mode for applying, from the LC resonator 84, a relatively weak magnetic field M which can be detected by the detecting LC resonator 94 and the energy detector 96 of the wireless power receiver 49. Therefore, the power consumption of the power feeder 25 is kept at a low level.

In the electronic cassette 24, the energy detector 96 supplies a feeding area detection signal to the data manager 106. In response to the feeding area detection signal, the data manager 106 receives the ID information of the power feeder 25 which is stored in the power feeding information manager 128 from the console 28, and transmits the wireless feeding enable signal to the cassette information manager 126 of the console 28.

The energy detector 96 also supplies the feeding area detection signal to the operation manager 102. In response to the feeding area detection signal, the operation manager 102 turns on the electronic cassette 24 to make it ready for use, thereby completing preparations for image capturing. Of course, the electronic cassette 24 may have, for example, on a side thereof, a power supply switch, not shown, which can be operated by the surgeon 18 or the radiological technician.

After the preparations for image capturing have been completed, the cassette controller 46 and the power feeding information manager 128 (and the cassette information manager 126) manages the remaining power level of the battery 44 to determine whether the remaining power level is sufficient or not, i.e., whether the battery 44 needs to be charged or not, in step S2. If it is judged that the battery 44 needs to be charged ("NO" in step S2), then the power feeding information manager 128 sends a power feeding start signal to the power feeding controller 86 of the power feeder 25. More specifically, the charging controller 108 of the cassette controller 46 sends the feeding start signal to the power feeding information manager 128 through the transceivers 48, 116, and the power feeding information manager 128 transfers the received feeding start signal to the feeding controller 86 through the transceivers 116, 82.

The power feeder 25 now supplies electric power to the electronic cassette 24, i.e., charges the battery 44 of the electronic cassette 24 with a desired amount of electric power at a desired timing in step S3. If the remaining power level of the battery 44 runs low during the surgical operation, then the battery 44 may be charged while it is being kept in the given image capturing position. If the remaining power level of the battery 44 runs low during the preparations for image capturing, i.e., while the electronic cassette 24 is being placed in position, or before radiographic images start being captured, then the battery 44 can be charged in a contactless (wireless) fashion immediately before or after the surgical operation is started, so that the preparations for image capturing can be completed quickly.

For contactlessly (wirelessly) supplying electric power to the electronic cassette 24, the power feeder 25 may be energized to apply the magnetic field M from the LC resonator 84 to the electronic cassette 24 under given operating conditions for a stronger level than in the low output operation mode (high output operation mode, power feeding operation mode). In the electronic cassette 24, the energy received by the detecting LC resonator 94 as well as the energy received by the LC resonator 88, may be used to charge the battery 44 through the charging circuit 90, for thereby quickly charging the battery 44.

The image capturing system 10 allows the console 28 to confirm the ID information of the power feeder 25 that is associated with the electronic cassette 24. Accordingly, even if the image capturing system 10 includes a plurality of power feeders that are selectively usable, the electronic cassette 24 can be appropriately and selectively supplied with electric power from a desired selected one of the power feeders based on the ID information confirmed by the console 28. As a result, wasteful power consumption and erroneous operation can be avoided.

If it is judged that the remaining power level of the battery 44 is sufficient ("YES" in step S2), then the image capturing controller 109 transmits an image-capturing permission signal (step S4) and the charging controller 108 transmits a feeding inhibition signal (step S5). Therefore, the image capturing apparatus 22 is brought into an image capturing start standby state capable of capturing radiographic images under the control of the console 28 (the image capturing condition manager 118 and the power feeding information manager 128), and the power feeder 25 is brought into a feeding inhibition state.

Consequently, while a radiographic image is being captured, the electronic cassette 24 is prevented from being contactlessly (wirelessly) supplied with electric power. Therefore, the voltage supplied from the battery 44 to the radiation detector 40 is prevented from becoming unstable and fluctuating greatly, and noise caused by the magnetic field M applied from the power feeder 25 is prevented from adversely affecting the radiation detector 40, so that a captured radiographic image is effectively prevented from suffering from noise and decreasing in quality.

In step S6, the surgeon 18 or the radiological technician moves the image capturing apparatus 22 to a position facing the electronic cassette 24, and then turns on the image capturing switch 72 to capture a radiographic image of the patient 14. The image capturing switch 72 comprises a two-stage switch including first and second stages, for example. The first stage starts up the radiation source 74 at a given tube current, and then the second stage operates the radiation source 74 to emit the radiation X.

When the surgeon 18 or the radiological technician operates the image capturing switch 72, the radiation source controller 78 of the image capturing apparatus 22 sends a request to the console 28 for sending the image capturing conditions. Based on the received request, the console 28 sends the image capturing conditions for an area to be imaged of the patient 14 which are registered in the image capturing condition manager 118 and the number of radiographic images to be captured, to the image capturing apparatus 22. When the radiation source controller 78 receives the image capturing conditions, it controls the radiation source 74 to apply radiation X at a given dose to the patient 14 according to the image capturing conditions. The image capturing conditions may be sent in advance from the console 28 to a memory, not shown, in the radiation source controller 78.

The radiation X which has passed through the patient 14 is applied to the grid 38, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges (signal charges), which represent radiographic image information of the patient 14, are read from the storage capacitors 53 according to address signals which are supplied from the address signal generator 98 of the cassette controller 46 to the line scanning driver 58 and the multiplexer 66.

Specifically, in response to the address signal supplied from the address signal generator 98, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 98, the address decoder 68 of the multiplexer 66 outputs a selection signal that successively turns the switches SW2 on in order to switch between the signal lines 56, for thereby reading the electric charges stored in the storage capacitors 53 of the pixels 50 connected to the selected gate line 54, through the signal lines 56.

The electric charges read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiographic image signal to the A/D converter 70, which converts the radiographic image signal into a digital signal (step S7). The digital signal which represents the radiographic image information is stored in the image memory 100 of the cassette controller 46.

Similarly, the address decoder 60 of the line scanning driver 58 successively turns on the switches SW1 to switch between the gate lines 54 according to the address signal supplied from the address signal generator 98. The electric charges stored in the storage capacitors 53 of the pixels 50 connected to the successively selected gate lines 54 are read through the signal lines 56, and processed by the multiplexer 66 and the A/D converter 70 into digital signals (step S7), which are stored in the image memory 100 of the cassette controller 46.

In this case, the end-of-A/D-conversion determining unit 107 determines whether the A/D conversion of radiographic image information by the A/D converter 70 is ended or not (step S8). When the end-of-A/D-conversion determining unit 107 has judged that the A/D conversion is ended (YES in step S8), the charging controller 108 determines charging of the battery 44 at the first charging intensity, and generates the feeding permission signal for permitting the power feeder 25 to supply the electronic cassette 24 with electric power (step S9). Also, when the charging controller 108 determines charging of the battery 44 at the first charging intensity, the charging intensity switching unit 113 generates the first charging control signal for controlling the power feeder 25 to charge the battery 44 at the first charging intensity.

The transceiver 48 sends the ID information of the power feeder 25, the feeding permission signal and the first charging control signal to the feeding information manager 128 of the console 28.

When receiving them, the feeding information manager 128 transfers the received ID information of the power feeder 25, the received feeding permission signal and the received first charging control signal to the power feeder 25. When the power feeder 25 receives them, the feeding controller 86 of the power feeder 25 controls the power feeder 25 to start feeding of the electronic cassette 24 and charge the battery 44 at the first charging intensity on the basis of the received feeding permission signal and first charging control signal (step S10). The first charging intensity is a charging intensity that is lower than the charging intensity (e.g., second charging intensity) in wireless power-feeding of step S3, and such that noise due to charging of the battery 44 does not adversely affect the digital radiographic image information converted by the A/D converter 70. Thus, the analog radiographic image information which is susceptible to noise is prevented from being adversely affected by noise which is caused by the wireless power feeding by the power feeder 25. Thus, it is possible to acquire radiographic image information of high quality. The digital radiographic image information, which is modestly susceptible to noise though not to the extent of the analog information, is also prevented from being adversely affected by noise due to wireless power-feeding.

When the end-of-A/D-conversion determining unit 107 judges that the A/D conversion has been not ended yet (NO in step S8), the charging controller 108 does not perform the process of step S9.

Next, in step S11, the end-of-information-delivery determining unit 111 determines whether transfer of the digital radiographic image information from the A/D converter 70 to the image memory 100 is ended or not. When the end-of-information-delivery determining unit 111 judges that the transfer has been ended (YES in step S11), the charging controller 108 determines charging of the battery 44 at the second charging intensity (e.g., charging intensity for wireless power-feeding at a high-power level) which is higher than the first charging intensity. When the charging controller 108 determines charging of the battery 44 at the second charging intensity, the charging intensity switching unit 113 generates the second charging control signal for controlling the power feeder 25 to charge the battery 44 at the second charging intensity.

The transceiver 48 sends the ID information of the power feeder 25 and the second charging control signal to the power feeding information manager 128 of the console 28.

When the feeding information manager 128 receives them, the feeding information manager 128 transfers the received ID information and second charging control signal to the power feeder 25. When the power feeder 25 receives them, the feeding controller 86 of the power feeder 25 switches the charging intensity at which the power feeder 25 is charging the electronic cassette 24, from the first charging intensity to the second charging intensity on the basis of the received second charging control signal, and then the battery 44 is charged at the second charging intensity (step S12).

When the end-of-information-delivery determining unit 111 judges that transfer of the radiographic image information form the A/D converter 70 to the image memory 100 has been not ended yet (NO in step S11), the charging controller 108 does not perform the process of step S12.

The radiographic image information represented by the digital signals stored in the image memory 100 is transmitted to the console 28 by way of wireless communications. The radiographic image information transmitted to the console 28 is received by the transceiver 116, processed by the image processor 120, and then stored in the image memory 122 in association with the patient information of the patient 14 registered in the patient information manager 124.

The radiographic image information processed by the image processor 120 is transmitted from the console 28 to the display device 26. In the display device 26, the receiver 110 receives the radiographic image information, and the display controller 112 controls the display unit 114 to display a radiographic image based on the radiation image information. The surgeon 18 can perform the surgical operation on the patient 14 while visually confirming the radiographic image displayed on the display unit 114.

Even if the remaining power level of the battery 44 of the electronic cassette 24 runs low due to radiographic images captured during the surgical operation, since the electronic cassette 24 is contactlessly (wirelessly) supplied with electric power from the power feeder 25, the battery 44 of the electronic cassette 24 can be charged with the electronic cassette 24 being kept in the image capturing position.

Unlike the operation in the flowchart of FIG. 6, the end-of-information-delivery determining unit 111 may determine whether storage of the digital radiographic image information into the image memory 100 is ended or not, and when the end-of-information-delivery determining unit 111 judges that storage of the digital radiographic image information into the image memory 100 has been ended, the charging controller 108 may determine charging of the battery 44 at the second charging intensity. In this case, during data storage to the image memory 100, during which data may be susceptible to noise though not as significantly as during the A/D conversion, the data are effectively prevented from being adversely affected by noise which may be caused by the contactless (wireless) electric power transmission from the power feeder 25 to the electronic cassette 24, and hence from being corrupted.

Alternatively, the end-of-information-delivery determining unit 111 may determine whether transmission of the digital radiographic image information from the image memory 100 to the console 28 through the transceivers 48, 116 is ended or not, and when the end-of-information-delivery determining unit 111 judges that the transmission is ended, the charging controller 108 may determine charging of the battery 44 at the second charging intensity. Thereby, the image data can be more effectively prevented from being adversely affected by noise which may be caused by the contactless (wireless) electric power feeding.

As described above, even though the feeding inhibition signal is generated (step S5) to inhibit the power feeding before the capture of a radiographic image, the image capturing system 10 can quickly start (resume) supplying electric power to the battery 44 after the A/D conversion has been finished (step S10), i.e., at a time when the radiographic image information is relatively less susceptible to noise. This is particularly effective when the battery 44 needs to be quickly charged for the next image capturing process after the remaining power level thereof has been greatly reduced in the previous image capturing process. If another image capturing process is to be performed after the sequence of steps S1 through S12, then control may return from step S12 to step S1.

The image capturing system 10 may be configured to charge the battery 44 under the control of the console 28 at desired times other than when radiographic images are captured.

In the above explanations, the number of images to be captured is assumed to be one. In a case where the number of images to be captured is plural, as shown in the flowchart in FIG. 7, the process of step S7 (application of radiation X and the A/D conversion of the detected radiographic image information) is performed until a given number of radiographic images to be captured are captured, i.e., until the radiation X is applied to the subject 14 by the given number of times (step S13). When the given number of images has been captured (YES in step S13), the determination process in step S8 is performed.

As described above, the image capturing system 10 according to the first embodiment controls charging of the battery 44 by the power feeder 25 based on whether the radiographic images of the patient 14 have been captured or not and/or whether delivery of the radiographic image information from the radiation detector 40 has been performed or not. Thus, noise due to charging of the battery 44 is prevented from adversely affecting the radiographic image information, and then it is possible to obtain radiographic image information of high quality. Additionally, it is possible to charge the battery 44 efficiently without adverse influences on the radiographic image information.

Specifically, when the A/D conversion of radiographic image information is ended, the power feeder 25 is controlled to charge the battery 44 at the first charging intensity. Thereafter, when any one of transfer of the radiographic image information from the A/D converter 70 to the image memory 100, storage of the radiographic image information into the image memory 100, and output of the radiographic image information from the image memory 100 to the console 28 is ended, the power feeder 25 is controlled to charge the battery 44 at the second charging intensity which is higher than the first charging intensity. That is, the image capturing system according to the embodiment has multiple charging intensity levels (first and second charging intensities in this case), and the charging intensity is optimized depending on the operational state of the electronic cassette 24.

Consequently, the power feeder 25 does not charge the battery 44 until the A/D conversion is ended, and the power feeder 25 starts charging the battery 44 after the A/D conversion has been ended. Thus, noise due to charging is prevented from adversely affecting radiographic image information during the A/D conversion in which analog radiographic image information, which is susceptible to noise, is converted into digital radiographic image information, whereby radiographic image information of high quality can be obtained.

During transfer, storage or transmission of digital radiographic image information which is less susceptible to noise, the battery 44 is charged at a charging intensity of low level (first charging intensity). On the other hand, after the end of the transfer, the storage or the transmission thereof, the battery 44 is charged at a charging intensity of high level (second charging intensity). Thus, noise is prevented from adversely affecting the digital radiographic image information during the transfer, the storage or the transmission, and the battery 44 can be charged efficiently without adverse influences on the digital radiographic image information.

In this case, when the end-of-A/D-conversion determining unit 107 judges that the A/D conversion is ended, the charging controller 108 generates the charging permission signal for permitting the power feeder 25 to charge the battery 44. When the charging controller 108 determines charging of the battery 44 at the first charging intensity, the charging intensity switching unit 113 generates the first charging control signal for controlling the power feeder 25 to charge the battery 44 at the first charging intensity. On the other hand, when the charging controller 108 determines charging of the battery 44 at the second charging intensity, the charging intensity switching unit 113 generates the second charging control signal for controlling the power feeder 25 to charge the battery 44 at the second charging intensity.

Further, when the transceiver 48 receives the image-capturing start signal indicating that application of radiation X to a patient 14 is started, the charging controller 108 generates the charging inhibition signal for inhibiting the power feeder 25 from charging the battery 44. When the transceiver 48 receives the image-capturing start signal, the image capturing controller 109 generates the image-capturing permission signal for permitting application of radiation X.

The transceiver 48 receives the image-capturing start signal, and sends the feeding permission signal, the first and second charging control signals, the feeding inhibition signal and the image-capturing permission signal, to the console 28.

Thus, information on permission of charging of the battery 44, charging of the battery 44 at the first charging intensity, charging of the battery 44 at the second charging intensity, inhibition of charging of the battery 44, and permission for the image capturing apparatus 22 to capture images is reliably transmitted from the electronic cassette 24 to the console 28, and also transmitted to the image capturing apparatus 22, the power feeder 25 and the display device 26 through the console 28. As a result, noise is reliably prevented from adversely affecting radiographic image information, and the battery 44 can be charged more efficiently.

Further, since the power feeder 25 contactlessly (wirelessly) supplies electric power to the battery 44 of the electronic cassette 24, even though the electronic cassette 24 is placed in a desired image capturing position with respect to the patient 14, the power feeder 25 can easily supply electronic power to the electronic cassette 24. Even if the battery 44 of the electronic cassette 24 needs to be charged during the surgical operation, the battery 44 can be charged without the need for moving the electronic cassette 24. Accordingly, the electronic cassette 24 and the image capturing system 10 can be handled with ease as a whole. Furthermore, the process of capturing a radiographic image and the surgical operation are effectively prevented from being interrupted and prolonged due to a low remaining power level of the battery 44 of the electronic cassette 24.

In the image capturing system 10 (the electronic cassette 24), a feeding inhibition signal is generated when an image-capturing permission signal is generated, and a feeding permission signal is generated after the A/D conversion of radiographic image information has been ended. Accordingly, the contactless (wireless) power feeding is inhibited at least from the start of image-capturing until the conversion of the analog radiographic image information detected by the radiation detector 40 into digital signals is completed. As a result, the analog radiographic image information, which is susceptible to noise, is prevented from being adversely affected by noise caused by the contactless (wireless) power feeding from the power feeder 25. Therefore, it is possible to acquire radiographic images of high quality.

After the A/D conversion, i.e., at a time when radiographic image information is relatively less susceptible to noise, the power feeder 25 quickly starts (resumes) the power feeding in response to a feeding permission signal from the charging controller 108. Therefore, even if the remaining power level of the battery 44 is greatly lowered by an image capturing process, the battery 44 can quickly be charged after the image capturing process and made ready for a next image capturing process.

When the electronic cassette 24 is placed within the feeding area of the power feeder 25, the electronic cassette 24 and the power feeder 25 automatically exchanges information with each other through the console 28, and the electronic cassette 24 is automatically brought into a state capable of capturing a radiographic image. Consequently, the electronic cassette 24 is not required to have a manual power supply switch, and the surgeon 18 or the radiological technician is prevented from making a mistake not to capture a radiographic image by forgetting to operating such a manual power supply switch. Accordingly, the electronic cassette 24 and the image capturing system 10 can be handled with greater ease as a whole. If the energy detector 96 of the electronic cassette 24 does not detect the desired magnetic field M, then the data manager 106 may send a wireless feeding disable signal representing that the power feeder 25 can not supply the battery 44 with electric power, for example, to the cassette information manager 126, from which the wireless feeding disable signal is sent to the display device 26 for indicating to the surgeon 18 or the radiological technician that it is not possible to supply electric power from the power feeder 25 to the electronic cassette 24, on the display unit 114.

The image capturing system 10 according to the first embodiment is not limited in the above descriptions. The present invention may be modified as follows.

The operation manager 102 may comprise a determining unit instead of the end-of-A/D-conversion determining unit 107 and the end-of-information-delivery determining unit 111. The determining unit determines whether image-capturing with respect to a patient 14 has been performed or not, and/or whether delivery of radiographic image information from the radiation detector 40 has been performed or not. The charging controller 108 may control charging of the battery 44 by the power feeder 25 based on a judgment result by the determining unit.

In this case, when the determining unit judges that image-capturing with respect to a patient 14 is being performed, the charging controller 108 inhibits the power feeder 25 from charging the battery 44, and/or when the determining unit judges that radiographic image information is being delivered from the radiation detector 40, the charging controller 108 limits charging of the battery 44 by the power feeder 25 (i.e., controls the power feeder 25 to charge the battery 44 at the first charging intensity).

With this arrangement, the above advantageous effects can be obtained easily.

In another arrangement, when the charging controller 108 determines charging of the battery 44 at the first charging intensity, the charging intensity switching unit 113 controls the end-of-A/D-conversion determining unit 107 to transmit the judgment result that the A/D conversion is ended, from the electronic cassette 24 to the console 28. Also, when the charging controller 108 determines charging of the battery 44 at the second charging intensity, the charging intensity switching unit 113 controls the end-of-information-delivery determining unit 111 to output the judgment result that any one of transfer of radiographic image information from the A/D converter 70 to the image memory 100, storage of the radiographic image information into the image memory, and transmission of the radiographic image information from the image memory 100 to the console 28 is ended.

The judgment results correspond respectively to the first charging control signal and the second charging control signal. Accordingly, the console 28 and the like can judge easily that the battery 44 should be charged at the first charging intensity or the second charging intensity, by receiving the above judgment results.

Also, the charging controller 108 may generate the charging inhibition signal for inhibiting the power feeder 25 from charging the battery 44 in synchronization with application of radiation X to a patient 14. Also in this case, the advantageous effects due to generation of the charging inhibition signal are obtained easily.

Figure 8:
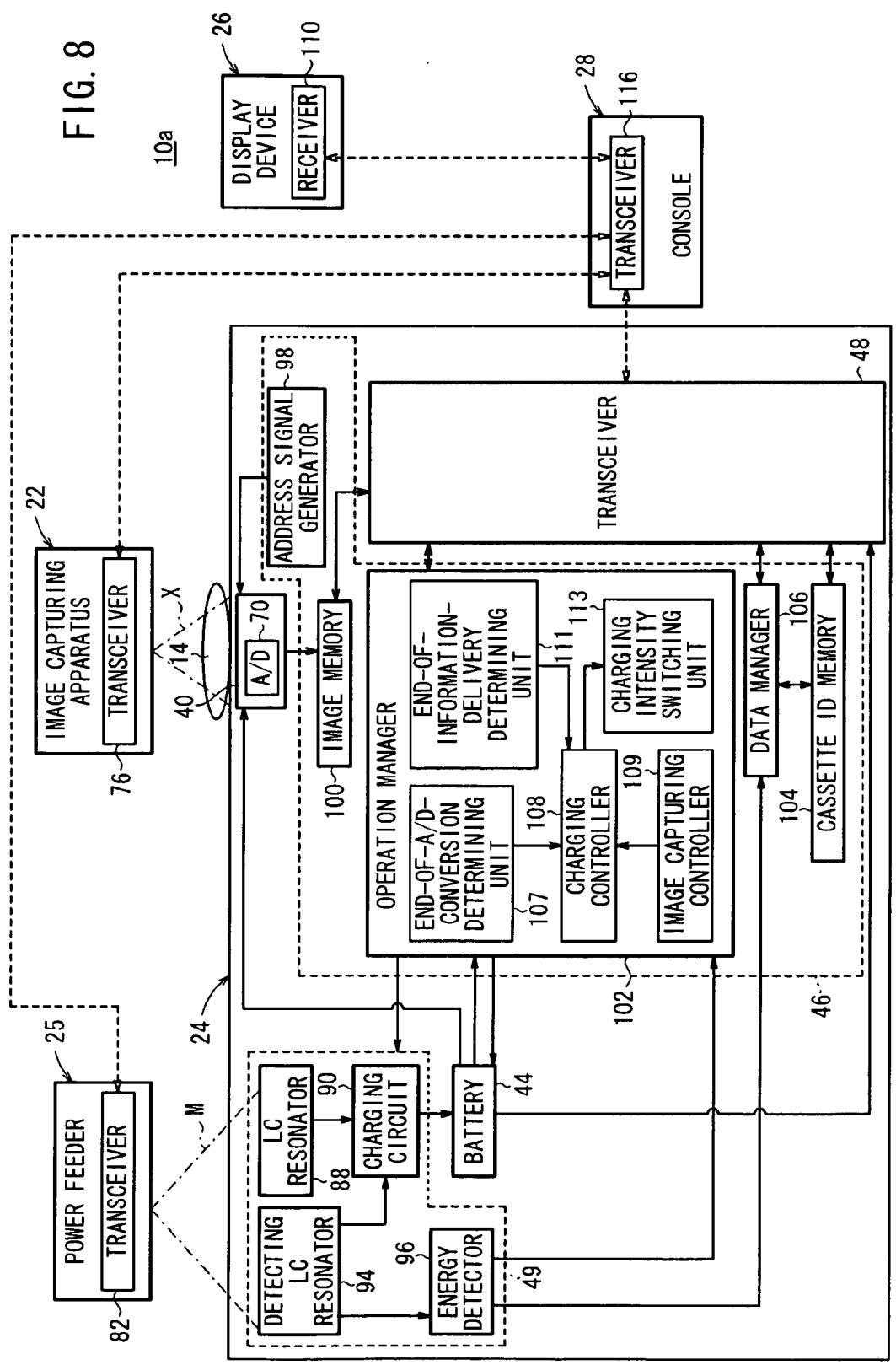
FIG. 8 is a block diagram of a radiographic image capturing system according to a second embodiment of the present invention.

FIG. 8 is a block diagram of a radiographic image capturing system 10*a* according to a second embodiment of the present invention.

As shown in FIG. 8, the radiographic image capturing system 10*a* according to the second embodiment is basically the same as the radiographic image capturing system 10 (see FIGS. 4 and 5) according to the first embodiment except that the RIS 29 and the HIS 33 are not connected to the console 28. The radiographic image capturing system 10*a* is preferably used as a radiographic image capturing system that is not connected to the RIS 29 and the HIS 33, e.g., a radiographic image capturing system in a hospital which is free of the RIS 29 and the HIS 33 or a radiographic image capturing system to accompany a doctor when going the rounds in a hospital.

In the image capturing system 10*a* or later, constituent elements thereof which are identical to those of the image capturing system 10 according to the first embodiment are denoted by like reference numerals, and detail explanations thereof are omitted.

Figure 7:
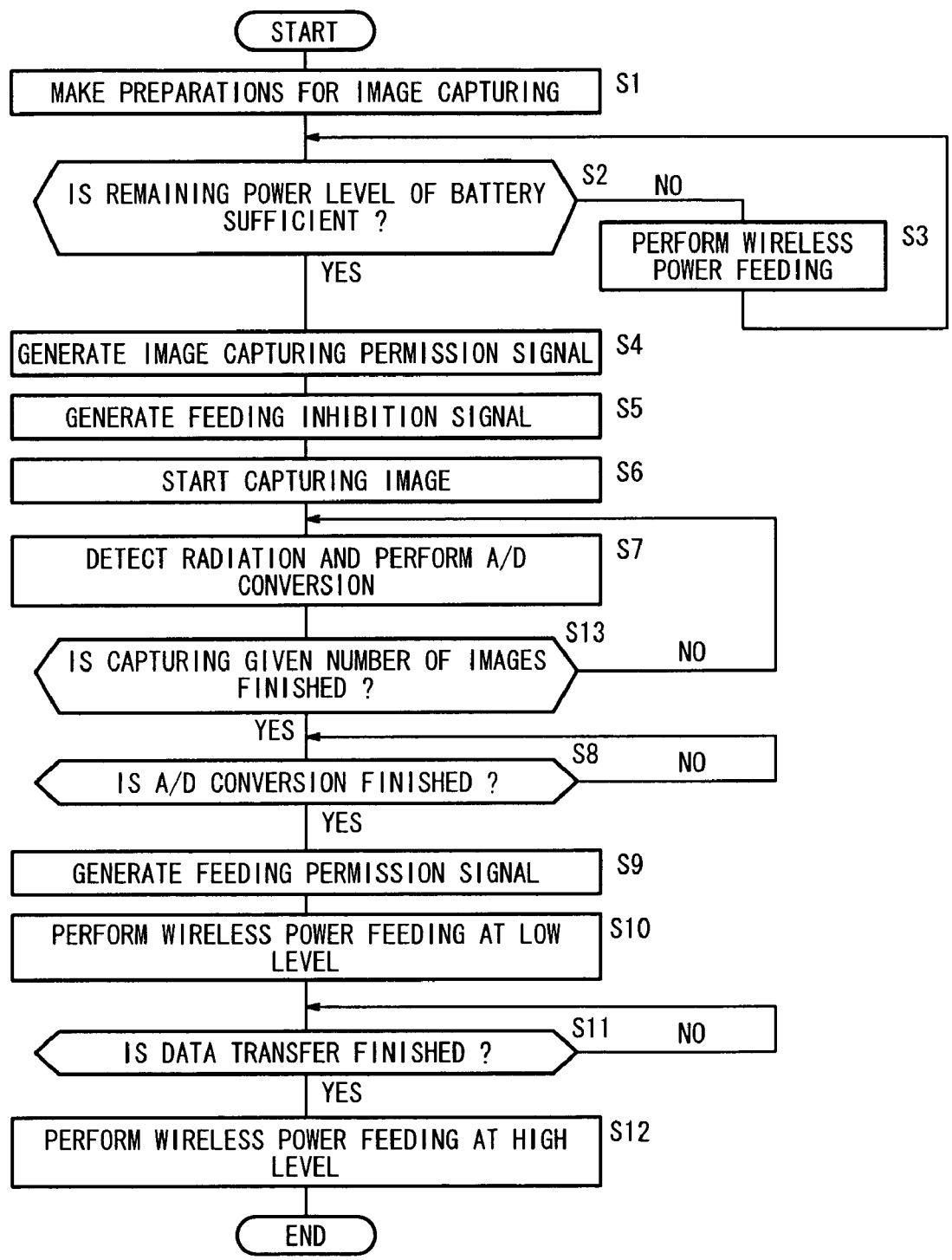
FIG. 7 is another flowchart showing a partial modification of the flowchart shown in FIG. 6.
Figure 9:
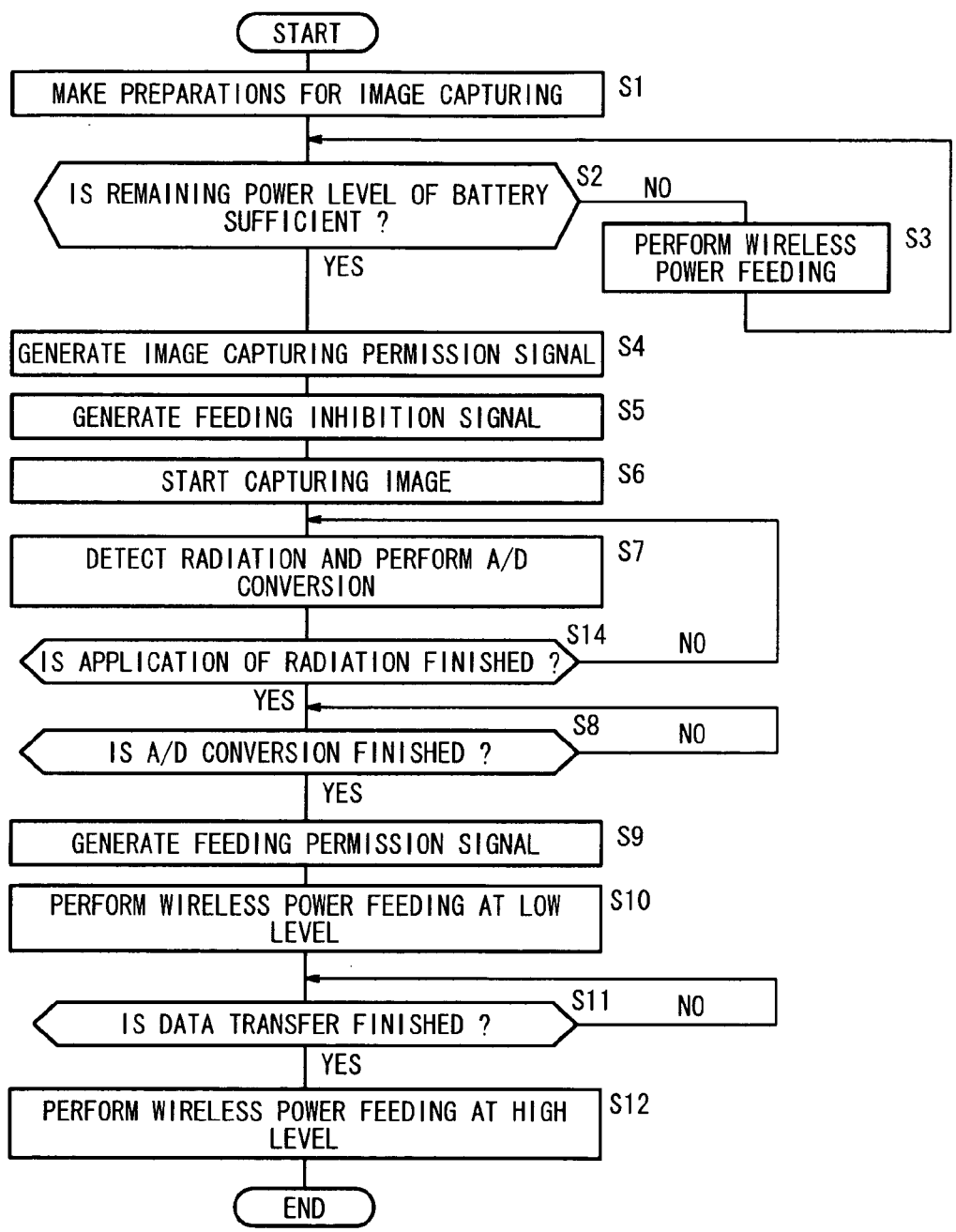
FIG. 9 is a flowchart of an image capturing sequence of the radiographic image capturing system shown in FIG. 8.

As shown in FIG. 9, the image capturing sequence of the radiographic image capturing system 10*a* is basically the same as the image capturing sequence of the image capturing system 10 shown in FIG. 7 except that step S14 is carried out instead of step S13 shown in FIG. 7.

Since the RIS 29 is not connected to the image capturing system 10*a*, the image capturing system 10*a* is unable to acquire ordering information about the number of times that the patient 14 is to be imaged (the number of radiographic images thereof to be captured, the number of times that the patient 14 is to be exposed to the radiation X). In step S14, it is determined whether the application of the radiation X by the image capturing apparatus 22 is finished or not, e.g., whether the image capturing switch 72 is turned off or not. If it is judged that the application of the radiation X is finished ("YES" in step S14), then information indicating that the image capturing switch 72 is turned off is supplied to the charging controller 108 under the control of the console 28. Thereafter, the determination process of step S8 is performed.

According to the image capturing system 10*a*, if it is judged that the application of the radiation X is finished ("YES" in step S14) and the A/D conversion is finished ("YES" in step S8), then the charging controller 108 generates a feeding permission signal in step S9. Therefore, even though the number of times that the patient 14 is to be imaged is not acquired from the RIS 29, the end of the capturing of the desired number of radiographic images can be judged from the stop of the application of the radiation X, e.g., the turning-off of the image capturing switch 72. Accordingly, noise caused by the wireless power feeding from the power feeder 25 is prevented from adversely affecting the analog radiographic image information.

Since the electronic cassette 24 has the operation manager 102, the image capturing system 10*a* can obtain the same advantageous effects as the image capturing system 10 according to the first embodiment.

Figure 10:
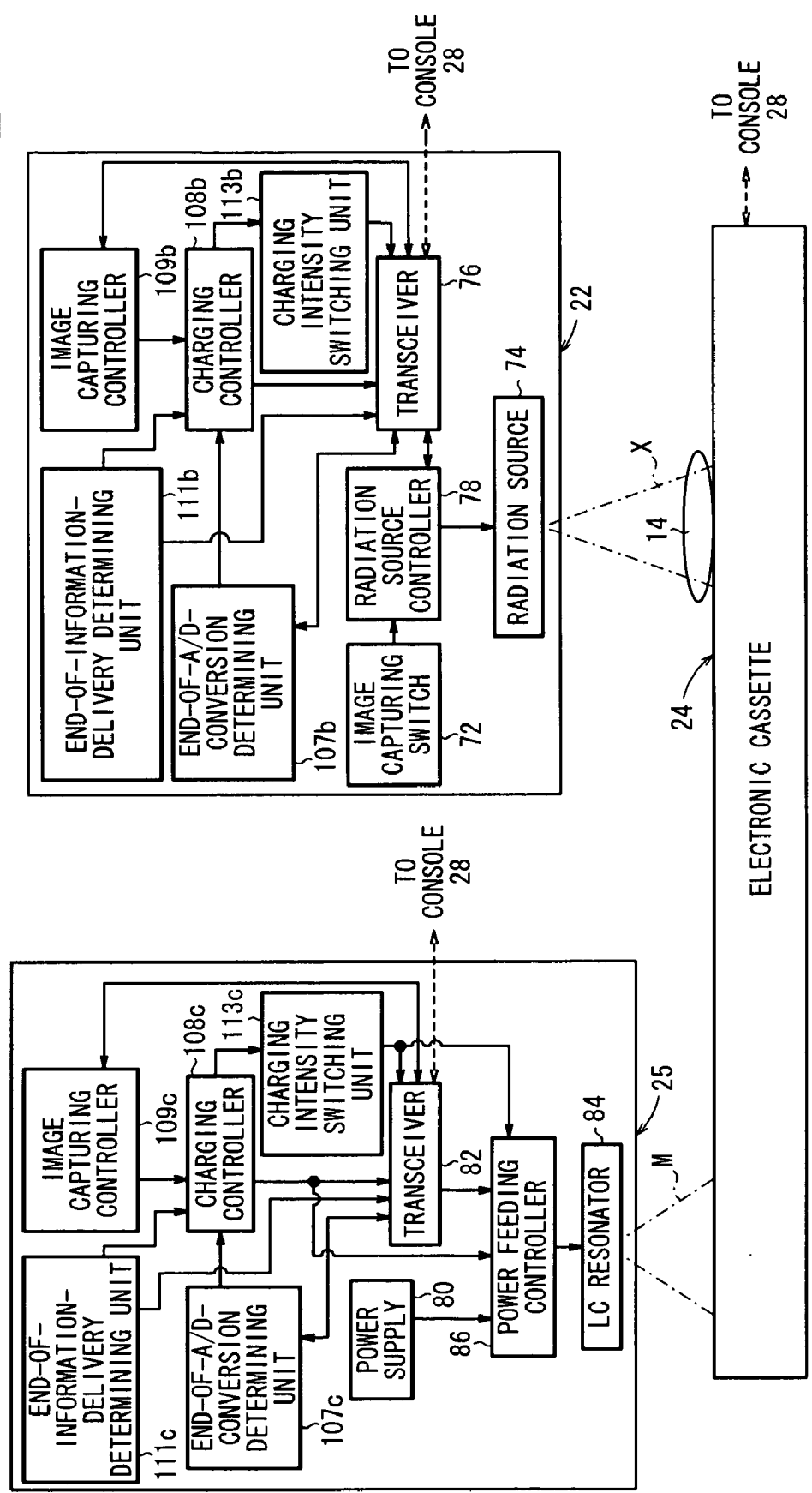
FIG. 10 is a block diagram of a radiographic image capturing system according to a first modification of the radiographic image capturing system shown in FIG. 4.
Figure 11:
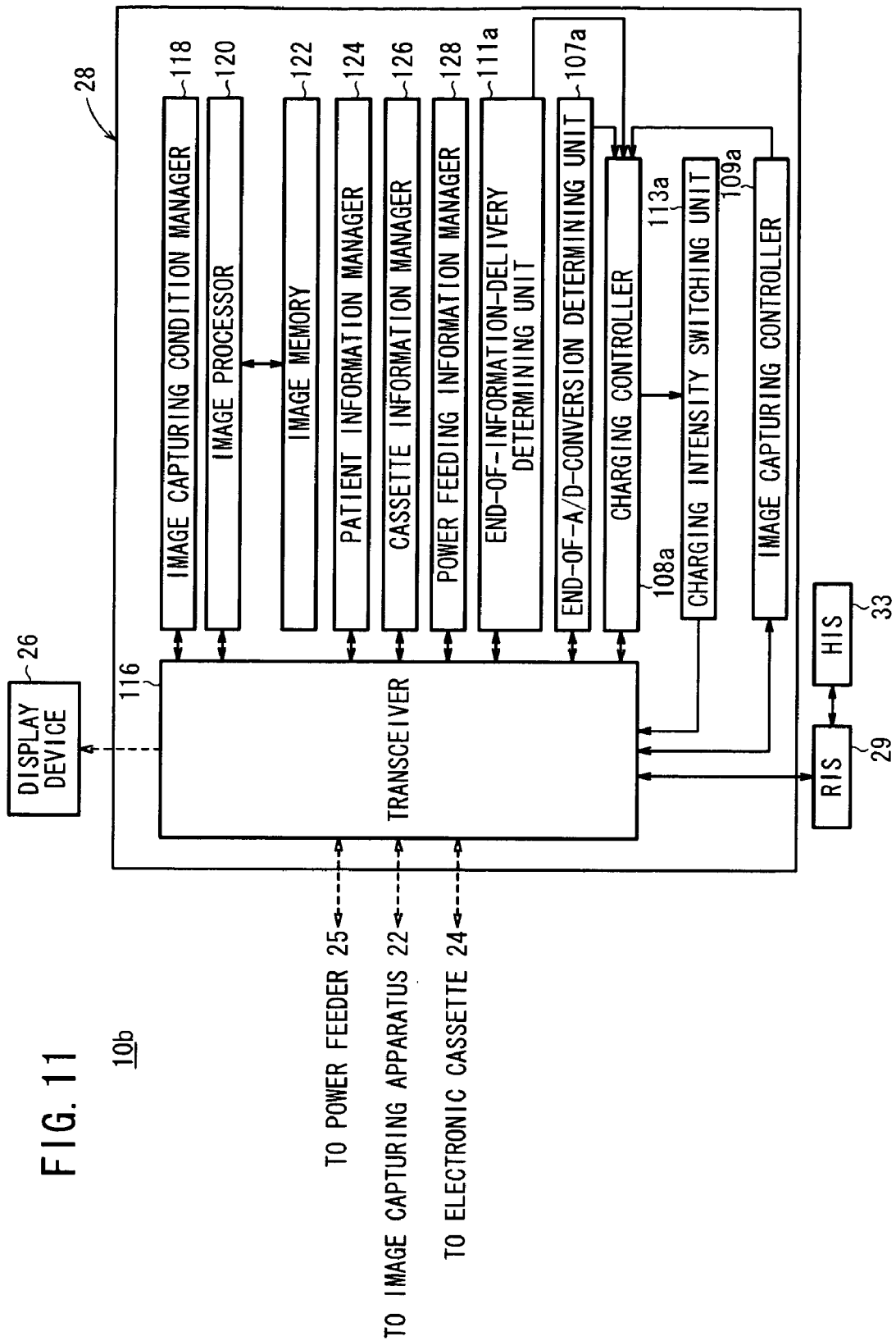
FIG. 11 is a block diagram of a radiographic image capturing system according to a first modification of the radiographic image capturing system shown in FIG. 4.

FIGS. 10 and 11 are a block diagram of a radiographic image capturing system 10b according to a first modification of the radiographic image capturing system 10 shown in FIG. 4.

The radiographic image capturing system 10b differs from the radiographic image capturing systems 10, 10a described above (see FIGS. 4, 5 and 8) in that an end-of-A/D-conversion determining unit 107a, a charging controller 108a, an image capturing controller 109a, an end-of-information-delivery determining unit 111a and a charging intensity switching unit 113a are incorporated in the console 28.

In the radiographic image capturing system 10b, the end-of-A/D-conversion determining unit 107a, the charging controller 108a, the image capturing controller 109a, the end-of-information-delivery determining unit 111a and the charging intensity switching unit 113a perform operations based on the image capturing sequence shown in FIG. 6 on the console 28 side. The end-of-A/D-conversion determining unit 107, the charging controller 108, the image capturing controller 109, the end-of-information-delivery determining unit 111 and the charging intensity switching unit 113 that are incorporated in the electronic cassette 24 may be disabled under the control of the console 28.

Alternatively, the radiographic image capturing system 10b may employ a simplified electronic cassette which is free of the end-of-A/D-conversion determining unit 107, the charging controller 108, the image capturing controller 109, the end-of-information-delivery determining unit 111 and the charging intensity switching unit 113.

As shown in FIGS. 10 and 11, an end-of-A/D-conversion determining unit 107b, a charging controller 108b, an image capturing controller 109b, an end-of-information-delivery determining unit 111b and a charging intensity switching unit 113b may be provided in the image capturing apparatus 22, in addition to or instead of the end-of-A/D-conversion determining unit 107a, the charging controller 108a, the image capturing controller 109a, the end-of-information-delivery determining unit 111a and the charging intensity switching unit 113a, and an end-of-A/D-conversion determining unit 107c, a charging controller 108c, an image capturing controller 109c, an end-of-information-delivery determining unit 111c and a charging intensity switching unit 113c may be provided in the power feeder 25. In other words, an end-of-A/D-conversion determining unit, a charging controller, an image capturing controller, an end-of-information-delivery determining unit and a charging intensity switching unit may be provided in at least either one of the console 28, the image capturing apparatus 22, the power feeder 25 and the electronic cassette 24 to allow the radiographic image capturing system 10b to operate in the same manner as the radiographic image capturing systems 10, 10a. The radiographic image capturing system 10b may include another dedicated console. If an end-of-A/D-conversion determining unit, a charging controller, an image capturing controller, an end-of-information-delivery determining unit and a charging intensity switching unit are provided in each of a plurality of apparatus, then the end-of-A/D-conversion determining unit, the charging controller, the image capturing controller, the end-of-information-delivery determining unit and the charging intensity switching unit provided in any one of the apparatus may selectively be used under the control of the console 28, for example, whereas the functions of the end-of-A/D-conversion determining unit, the charging controller, the image capturing controller, the end-of-information-delivery determining unit and the charging intensity switching unit provided in the other apparatus may be disabled.

Since the electronic cassette 24 incorporates the end-of-A/D-conversion determining unit 107, the charging controller 108, the image capturing controller 109, the end-of-information-delivery determining unit 111 and the charging intensity switching unit 113, the control function such as the above determination process may be added easily to an existing radiographic image capturing system simply by slightly modifying the control program of the console 28.

With the radiographic image capturing systems 10, 10a, 10b, radiographic images used in a surgical operation are displayed by the display device 26. However, the radiographic image capturing systems 10, 10a, 10b may be used to capture ordinary radiographic images in applications other than surgical operations. Similarly, the electronic cassette 24 is not limited to use in the operating room 12, but may be used in medical examinations or used by doctors when going the rounds in hospitals, for example.

As described in the above explanations of the first embodiment, the power feeder 25 may be of any type insofar as it can supply electric power contactlessly (wirelessly) to the electronic cassette 24. For example, the power feeder 25 may comprise components made of a dielectric material for utilizing an electric field (electric field resonance) rather than the magnetic field (magnetic resonance), rather than the LC resonators 84, 88 and the detecting LC resonators 94, and hence may be other than the resonant wireless power feeder. Stated otherwise, the electric energy supplied from the power feeder 25 to the electronic cassette 24 may be optical energy, thermal energy, or other types of energy.

In the radiographic image capturing systems 10, 10a, 10b, the radiation detector 40 housed in the electronic cassette 24 is a direct-conversion type radiation detector which directly converts the dose of the applied radiation X into an electric signal with the photoelectric conversion layer 51. However, the radiographic image capturing systems may employ a indirect-conversion type radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiographic image capturing systems may employ a light-readout type radiation detector for acquiring radiographic image information. The light-readout type radiation detector operates as follows: When radiation is applied to a matrix of solid-state detecting devices, the solid-state detecting devices store an electrostatic latent image depending on the dose of the applied radiation. For reading the stored electrostatic latent image, reading light is applied to the radiation detector, and the generated electric current values are acquired as radiation image information. When erasing light is applied to the radiation detector, radiographic image information representing a residual electrostatic latent image is erased from the radiation detector, which can thus be reused (see Japanese Laid-Open Patent Publication No. 2000-105297).

Signals may be sent and received between the image capturing apparatus 22, the power feeder 25, the display device 26, and the console 28 by way of wired communications. In the wired communications, which is modestly susceptible to noise though not to the extent of the wireless communications, noise caused by charging of the battery 44 is prevented from adversely affecting radiographic image information, whereby radiographic image information of high quality can be obtained. Wireless communications between the electronic cassette 24 and external equipment may be optical wireless communications based on infrared rays rather than ordinary radio-wave communications.

Figure 12:
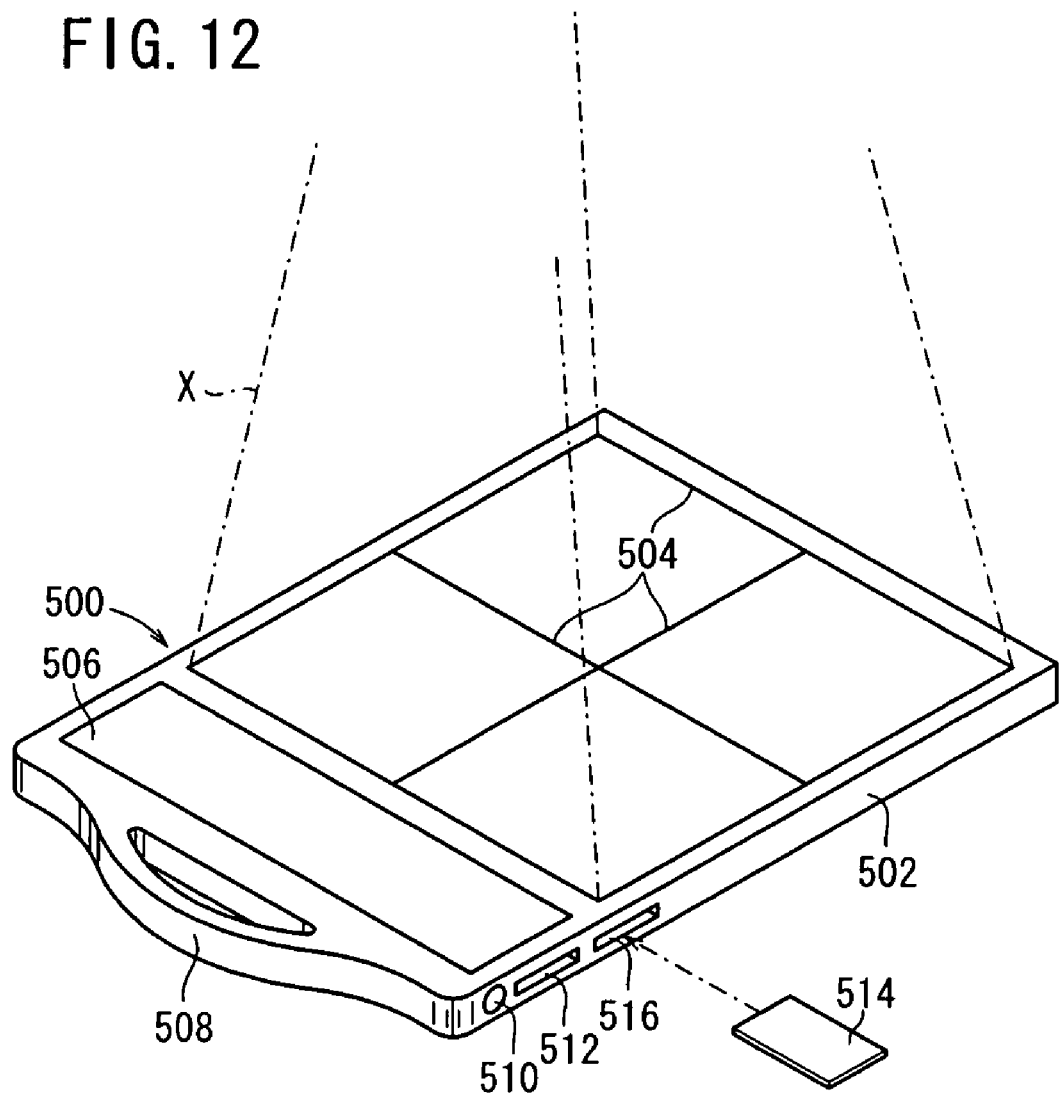
FIG. 12 is a perspective view of another electronic cassette.

FIG. 12 shows in perspective an electronic cassette 500 according to a modification of the electronic cassette 24.

As shown in FIG. 12, the electronic cassette 500 has guide lines 504 drawn on the irradiated surface of a casing 502 as a reference mark for an image capturing area and an image capturing position. Using the guide lines 504, the subject to be imaged, such as the patient 14, can be positioned with respect to the electronic cassette 500 and the range in which the radiation X is to be applied to the electronic cassette 500 can be determined, for thereby recording radiographic image information in an appropriate image capturing area of the electronic cassette 500.

The electronic cassette 500 also has a display unit 506 outside of the image capturing area thereof for displaying various items of information about the electronic cassette 500. Specifically, the display unit 506 displays ID information of the patient 14, whose radiation image is recorded in the electronic cassette 500, the number of times that the electronic cassette 500 has been used, an accumulated exposed dose, the charged state (remaining power level) of the battery 44 housed in the electronic cassette 500, image capturing conditions for radiographic image information, and a positioning image representing the patient 14 positioned with respect to the electronic cassette 500, etc. The radiological technician can confirm the patient 14 based on the ID information displayed on the display unit 506, also confirm in advance that the electronic cassette 500 is in a usable state, position the desired area to be imaged of the patient 14 with respect to the electronic cassette 500 based on the displayed positioning image, and capture optimum radiographic image information in the electronic cassette 500.

The electronic cassette 500 includes a handle 508 to be gripped by the user in order to handle and carry the cassette 500 with ease.

The cassette 500 also preferably has an input terminal 510 for connection to an AC adapter, a USB (Universal Serial Bus) terminal 512, and a card slot 516 for receiving a memory card 514, all provided on a side wall of the casing of the electronic cassette 500.

When the charging function of the battery 44 housed in the electronic cassette 500 is low or when there is not enough time to charge the battery 44, an AC adapter is connected to the input terminal 510 to supply electric power from an external source for thereby making the electronic cassette 500 immediately operable.

The USB terminal 512 or the card slot 516 can be used when the electronic cassette 500 is unable to send and receive information to and from an external device (external equipment) such as the console 28 or the like by way of wireless communication. Specifically, when a USB cable connected to the external device is connected to the USB terminal 512, the cassette 500 can send and receive information to and from the external device by way of wired communications through the USB terminal 512 and the USB cable. Alternatively, the memory card 514 is inserted into the card slot 516 and necessary information from the cassette 500 is recorded into the memory card 514. Thereafter, the memory card 514 is disconnected from the card slot 516 and then connected to the external device to send the information to the external device.

Figure 13:
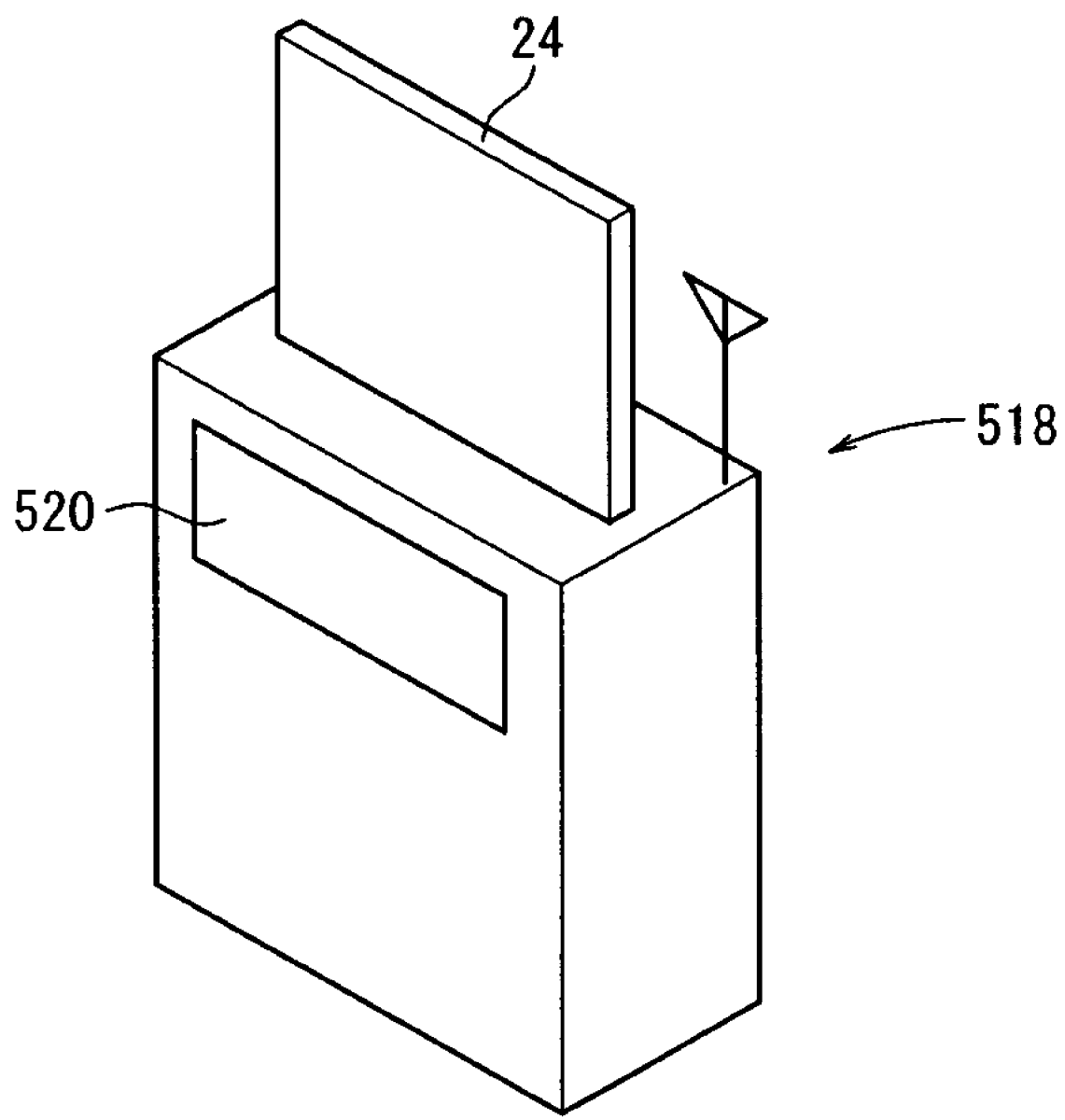
FIG. 13 is a perspective view of a cradle for charging a battery in the electronic cassette.

FIG. 13 shows a cradle 518 for receiving the electronic cassette 24 and charging the battery 44 housed in the electronic cassette 24. The cradle 518 should preferably be positioned in the operating room 12 or a desired location in the hospital. The cradle 518 may not only be able to charge the battery 44 with a contactless power feeder, not shown, similar to the above power feeder 25, but also have a wireless or wired communication function to send and receive necessary information to and from an external device (external equipment), such as the RIS 29, the HIS 33, the console 28, or the like. The information that is sent and received may include radiation image information recorded in the electronic cassette 24 loaded in the cradle 518.

The cradle 518 has a display unit 520 for displaying the charged state of the battery 44 housed in the electronic cassette 24 and necessary information including radiation image information acquired from the electronic cassette 24.

A plurality of cradles 518 may be connected to a network, and charged states of the batteries 44 housed in the electronic cassettes 24 loaded in the respective cradles 518 may be retrieved through the network, so that the user can confirm the locations of any electronic cassettes 24 whose batteries 44 are sufficiently charged, based on the retrieved charged states of the batteries 44.

Figure 14:
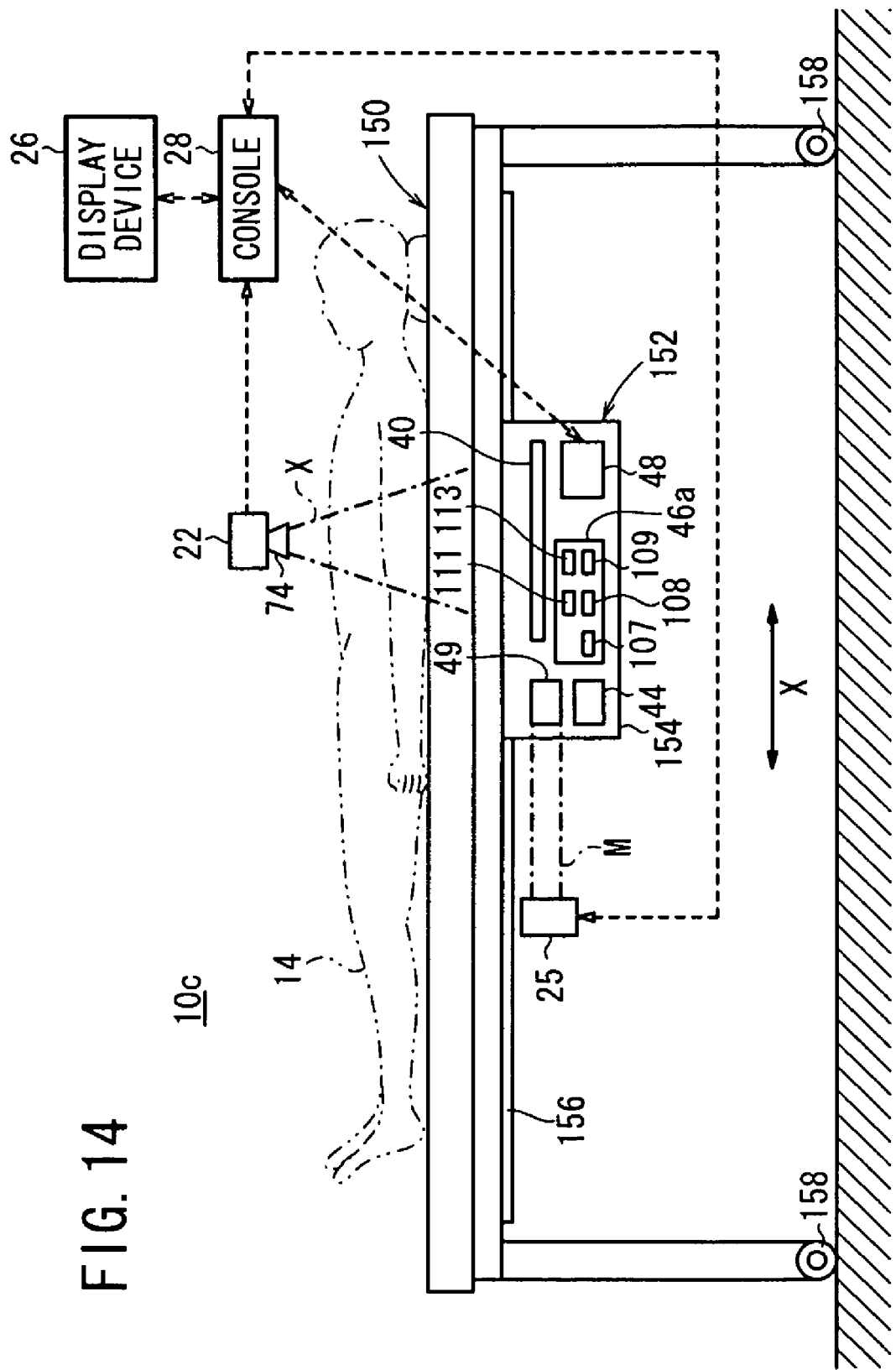
FIG. 14 is a side elevational view, partly in block form, of a radiographic image capturing system according to a second modification of the radiographic image capturing system shown in FIG. 4.

FIG. 14 is a side elevational view, partly in block form, of a radiographic image capturing system 10c according to a second modification of the radiographic image capturing system 10 shown in FIG. 4.

The above radiographic image capturing system 10 and the like employ the electronic cassette 24 as a radiation detecting apparatus for detecting the applied radiation X and acquiring radiographic image information. The radiographic image capturing system 10c shown in FIG. 14 employs, instead of the electronic cassette 24, a radiation detecting apparatus 152 incorporated in an image capturing table 150 for the patient 14 to lie thereon, for capturing a radiographic image of the patient 14 while the patient 14 is lying on the image capturing table 150.

The radiation detecting apparatus 152 is substantially the same in construction as the electronic cassette 24 and incorporates therein the radiation detector 40, the battery 44, the wireless power receiver 49, a controller 46a, and the transceiver 48, which are housed in a box-shaped casing 154 made of a material that is permeable to the radiation X. The controller 46a functions in substantially the same fashion as the cassette controller 46 of the electronic cassette 24, and has the end-of-A/D-conversion determining unit 107, the charging controller 108, the image capturing controller 109, the end-of-information-delivery determining unit 111 and the charging intensity switching unit 113.

A longitudinal rail 156 is mounted on a lower surface of the image capturing table 150. The radiation detecting apparatus 152 is movable to a desired position in the directions indicated by the arrow X (horizontal direction) along the rail 156 by a slider mechanism, not shown, mounted on the casing 154. Therefore, the radiation detecting apparatus 152 can be moved horizontally to a desired area to be imaged of the patient 14 lying on the image capturing table 150.

With the radiographic image capturing system 10c, the radiation detecting apparatus 152 is movable and incorporates the battery 44 and the wireless power receiver 49, as with the electronic cassette 24. Consequently, no power cable needs to be connected to the radiation detecting apparatus 152. The radiation detecting apparatus 152 can be moved smoothly without being limited by the power cable and hence can be handled with ease. As with the radiographic image capturing systems 10, 10a, 10b, the radiographic image capturing system 10c is capable of suitably controlling the contactless (wireless) power feeding from the power feeder 25 to the battery 44 and the image capturing by the image capturing apparatus 22 for thereby acquiring radiographic images of high quality.

As shown in FIG. 14, rollers 158 may be mounted on the lower ends of legs of the image capturing table 150. Therefore, the image capturing table 150 can easily be moved to a desired position. If necessary, the rail 156 may be dispensed with, and the radiation detecting apparatus 152 may be fixed to the image capturing table 150.

Figure 15:
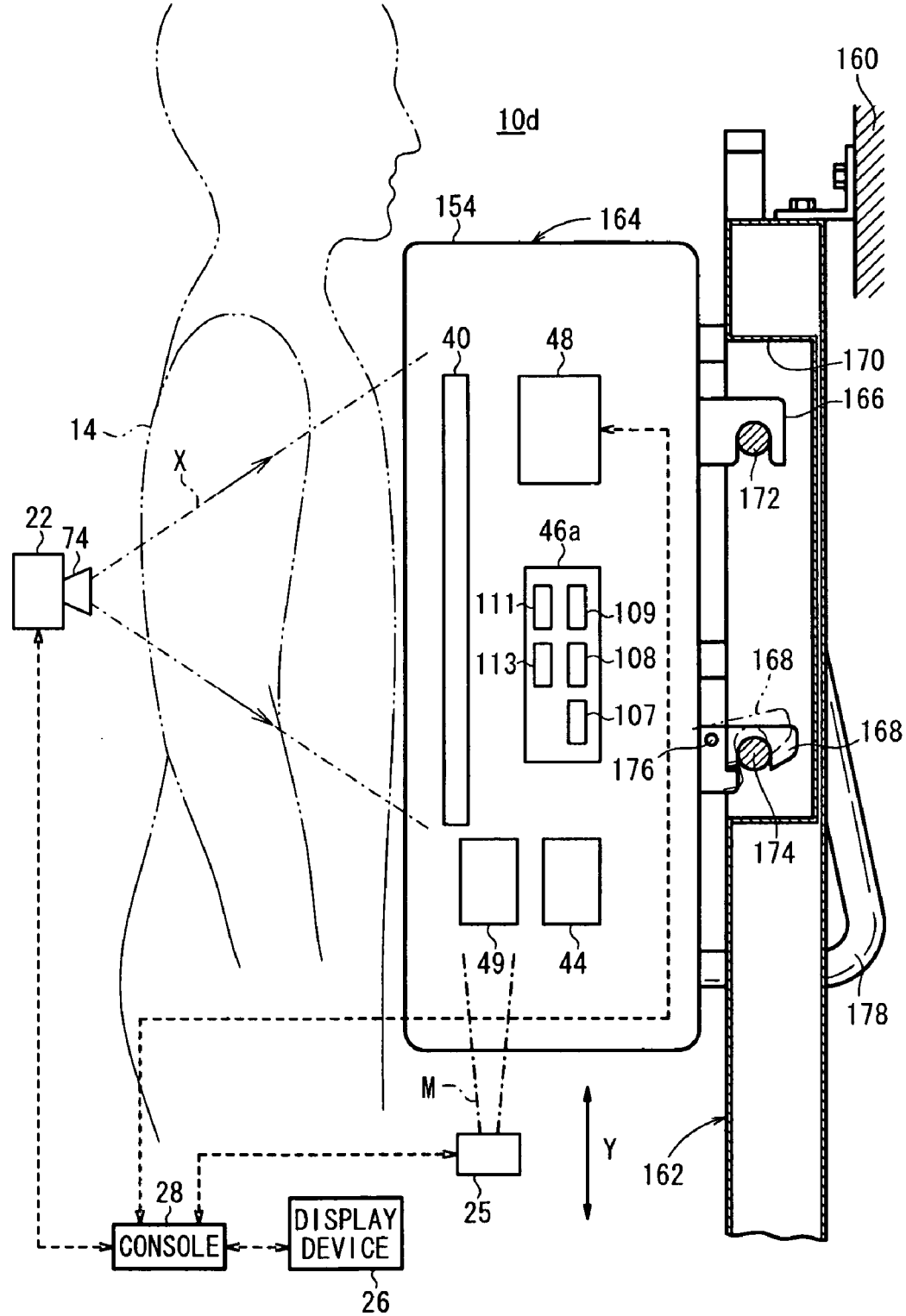
FIG. 15 is a side elevational view, partly in block form and cross section, of a radiographic image capturing system according to a third modification of the radiographic image capturing system shown in FIG. 4.

FIG. 15 is a side elevational view, partly in block form and cross section, of a radiographic image capturing system 10*d* according to a third modification of the radiographic image capturing system 10 shown in FIG. 4.

As with the radiographic image capturing system 10*c*, the radiographic image capturing system 10*d* does not employ the electronic cassette 24, but includes a radiation detecting apparatus 164 detachably mounted on a vertical post 162 fixed to a floor, not shown, and a wall 160, for capturing a radiographic image of the patient 14 while the patient 14 is upstanding.

The radiation detecting apparatus 164 is substantially the same in construction as the electronic cassette 24 and the radiation detecting apparatus 152 and incorporates therein the radiation detector 40, the battery 44, the wireless power receiver 49, the controller 46*a*, and the transceiver 48, which are housed in the box-shaped casing 154 made of a material that is permeable to the radiation X.

The radiation detecting apparatus 164, which functions as an upstanding image capturing table, has a pair of vertically spaced upper and lower hooks 166, 168 on a rear surface thereof which faces the post 162. The post 162 has a mounting recess 170 defined in a side surface thereof which faces the radiation detecting apparatus 164. A pair of vertically spaced upper and lower shafts 172, 174 for engaging the respective hooks 166, 168 are disposed in the mounting recess 170 and extend horizontally in transverse directions (shoulder-width direction) of the patient 14. The lower hook 168 is pivotally supported on a pivot shaft 176 for upward swinging movement about the pivot shaft 176 as indicated by the two-dot-and-dash lines in FIG. 15. The lower hook 168 is normally biased to turn downwardly by a spring mechanism, not shown, to stay in engagement with the lower shaft 174.

Since the hook 168 is swingably movable about the pivot shaft 176, the hooks 166, 168 can easily and reliably be brought into and out of hooking engagement with the respective shafts 172, 174, or in other words, the radiation detecting apparatus 164 can easily and reliably be mounted on and removed from the post 162. The radiation detecting apparatus 164 mounted on the post 162 can be moved vertically in the directions indicated by the arrows Y by a slide mechanism, not shown.

In FIG. 15, frames 178 are fixed to respective transverse ends of the casing 154. The frames 178 are in the form of rods to be gripped by the patient 14 when the patient 14 wants to take or keep a desired image capturing posture with respect to the radiation detecting apparatus 164.

With the image capturing system 10*d*, the radiation detecting apparatus 164 is removably mounted on and movable with respect to the post 162, and incorporates the battery 44 and the wireless power receiver 49 as with the electronic cassette 24 and the radiation detecting apparatus 152. Consequently, no power cable needs to be connected to the radiation detecting apparatus 164. The radiation detecting apparatus 164 can be moved, mounted and removed smoothly without being limited by the power cable. As with the radiographic image capturing systems 10, 10*a*, 10*b*, 10*c*, the radiographic image capturing system 10*d* is capable of suitably controlling the contactless (wireless) power feeding from the power feeder 25 to the battery 44 and the image capturing by the image capturing apparatus 22 for thereby acquiring radiographic images of high quality.

Figure 16:
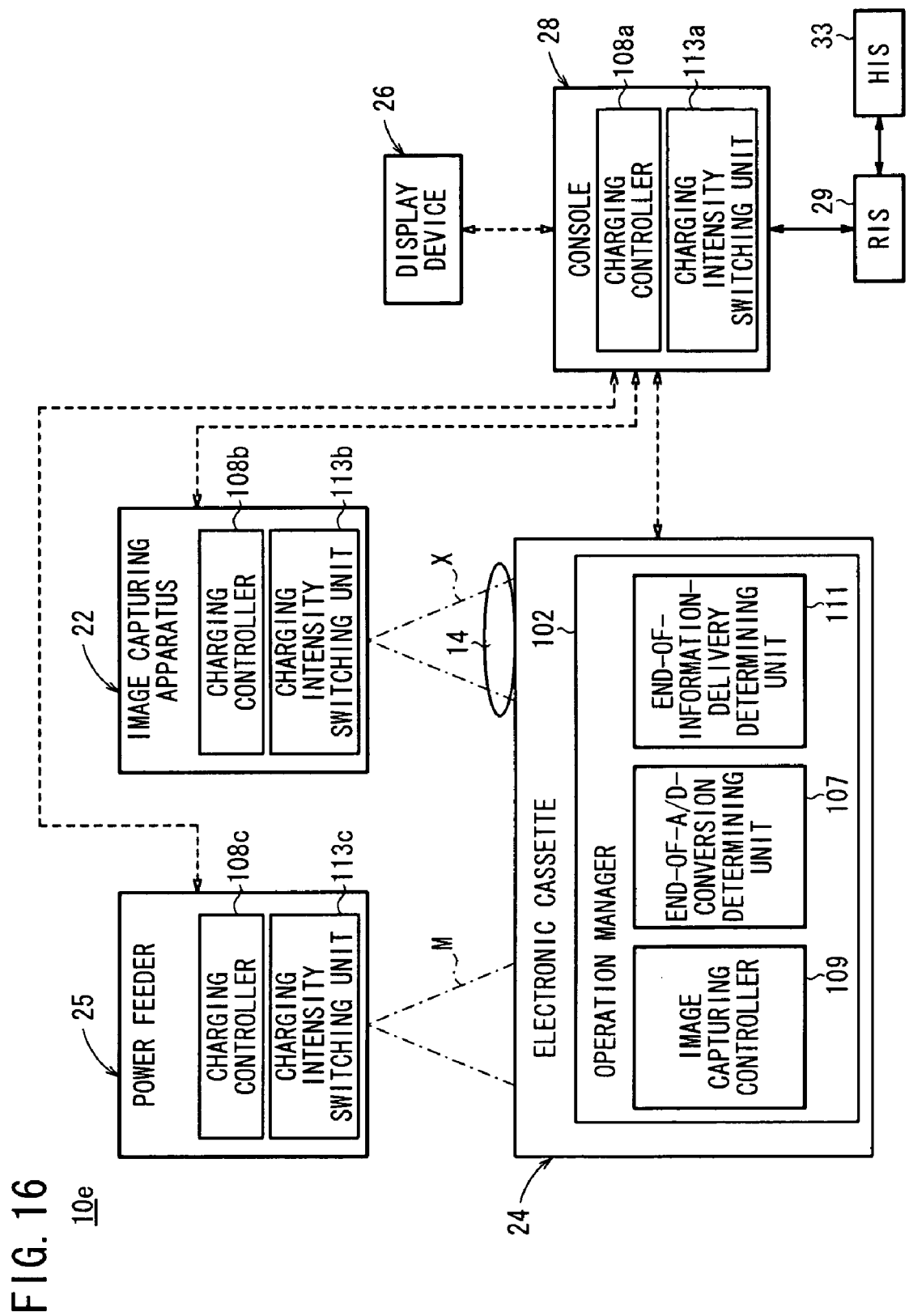
FIG. 16 is a schematic view of a radiographic image capturing system according to a fourth modification of the radiographic image capturing system shown in FIG. 4.

FIG. 16 is a schematic view of a radiographic image capturing system 10*e* according to a fourth modification of the radiographic image capturing system 10, 10*b* shown respectively in FIGS. 4, 10 and 11.

The radiographic image capturing system 10*e* differs from the radiographic image capturing system 10, 10*b* (see FIGS. 4, 10 and 11) in that the end-of-A/D-conversion determining unit 107, the image capturing controller 109 and the end-of-information-delivery determining unit 111 are provided in the operation manager 102, and the charging controllers 108*a*, 108*b*, 108*c* and the charging intensity switching units 113*a*, 113*b*, 113*c* are provided in the console 28, the image capturing apparatus 22 and the power feeder 25, respectively.

In FIG. 16, constituent elements other than the operation manager 102, the end-of-A/D-conversion determining unit 107, the image capturing controller 109 and the end-of-information-delivery determining unit 111 in the electronic cassette 24, and the charging controllers 108*a*, 108*b*, 108*c* and the charging intensity switching units 113*a*, 113*b*, 113*c* in the console 28, the image capturing apparatus 22 and the power feeder 25 are not illustrated.

In FIG. 16, the console 28, the image capturing apparatus 22 and the power feeder 25 have the charging controllers 108*a*, 108*b*, 108*c* and the charging intensity switching units 113*a*, 113*b*, 113*c*, respectively. However, any one thereof may have a charging controller and a charging intensity switching unit. That is, in the fourth modification, if the end-of-A/D-conversion determining unit, the image capturing controller, the end-of-information-delivery determining unit, the charging controller and the charging intensity switching unit are provided in at least two apparatus (two of the image capturing apparatus 22, the electronic cassette 24, the power feeder 25 and the console 28), the same functions as the operation manager 102 shown in FIG. 5 can be performed. Thus, the fourth modification is not limited to an example of FIG. 16. For example, one apparatus may have an end-of-A/D-conversion determining unit, an image capturing controller, an end-of-information-delivery determining unit and a charging controller, while another apparatus may have only a charging intensity switching unit.

In the image capturing system 10*e* of FIG. 16, the end-of-A/D-conversion determining unit 107, the image capturing controller 109 and the end-of-information-delivery determining unit 111 of the operation manager 102 recognize a state (operation mode) of the electronic cassette 24, and send a signal corresponding to the state to the charging controllers 108*a*, 108*b*, 108*c*. Then, the charging controllers 108*a*, 108*b*, 108*c* determine the most appropriate power feeding state (first charging intensity, second charging intensity, stoppage of charging) based on the operation mode (the sent signal), and the charging intensity switching units 113*a*, 113*b*, 113*c* generate control a signal corresponding to the determined most appropriate power feeding state.

The image capturing system 10*e* according to the fourth modification can obtain the same advantageous effects as the image capturing system 10 of the first embodiment and the image capturing system 10*b* of the first modification.

Figure 17:
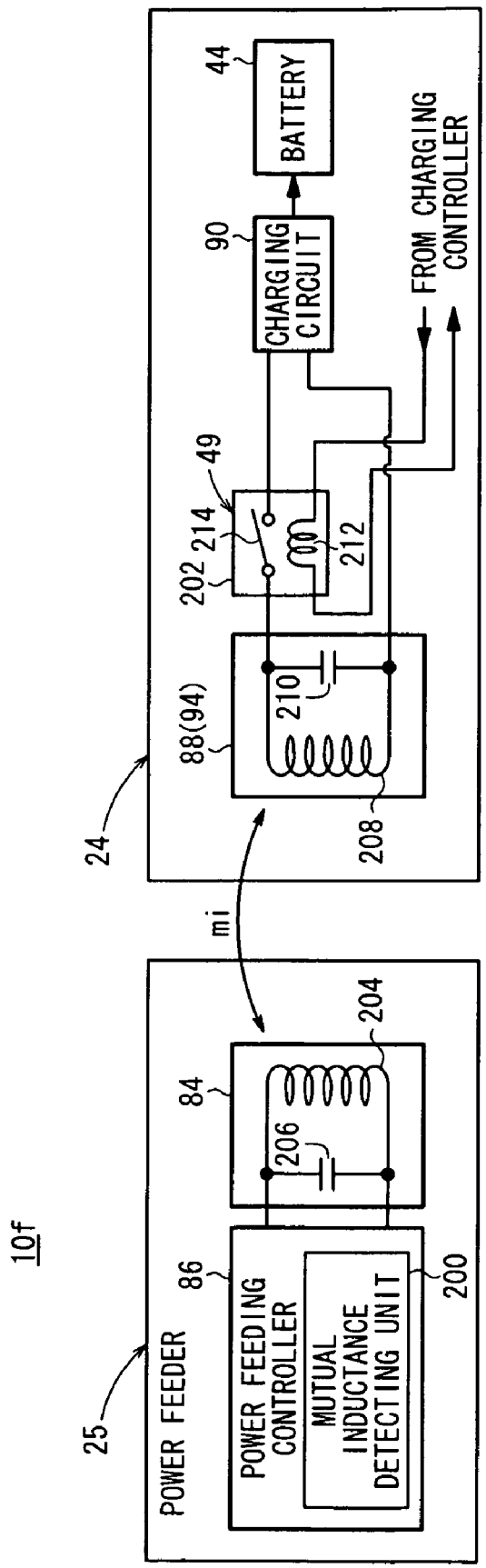
FIG. 17 is a schematic view of a radiographic image capturing system according to a fifth modification of the radiographic image capturing system shown in FIG. 4.

FIG. 17 is a schematic view of a radiographic image capturing system 10*f* according to a fifth modification of the radiographic image capturing system 10 shown in FIG. 4.

The image capturing system 10*f* differs from the image capturing system 10 (see FIGS. 4 and 5) according to the first embodiment in that the feeding controller 86 of the power feeder 25 has a mutual inductance detecting unit 200, and the wireless power receiver 49 has a relay 202. In FIG. 17, constituent elements other than the LC resonator 84 and the power feeding controller 86 of the power feeder 25, the battery 44 of the electronic cassette 24 and the wireless power receiver 49 are not illustrated.

In an example thereof, the LC resonator 84 of the power feeder 25 comprises an LC parallel resonant circuit having a coil 204 and a capacitor 206 that are connected together in parallel with each other, while the LC resonator 88 or the detecting LC resonator 94 of the electronic cassette 24 comprises an LC parallel resonant circuit having a coil 208 and a capacitor 210 that are connected together in parallel with each other. The relay 202 comprises an operation coil 212 to which the charging controller 108 supplies a signal (electric current), and a contact-type switch 214 for performing ON-OFF action in response to excitation of the operation coil 212 by the electric current. The switch 214 has an end connected to the coil 208 and the capacitor 210, and the other end connected to the charging circuit 90.

When the charging controller 108 determines charging of the battery 44 (charging at the first charging intensity or at the second charging intensity) and then applies electric current to the operation coil 212, the operation coil 212 generates magnetic flux based on the electric current, and magnetizes an electromagnet (not shown). As a result, the electromagnet attracts a piece of iron of the switch 214 to switch from an OFF-state to an ON-state. Thus, contactless power feeding by the power feeder 25 to the battery 44 (charging at the first charging intensity or at the second charging intensity) is enabled.

On the other hand, while the contactless power feeding is being performed, the coil 204 of the LC resonator 84 and the coil 208 of the LC resonator 88 or the detecting LC resonator 94 are magnetically-coupled to each other through a mutual inductance mi.

In this state, if the charging controller 108 determines stoppage (inhibition) of charging the battery 44 to stop energization of the operation coil 212, generation of magnetic flux by the operation coil 212 is halted.

Accordingly, the piece of iron is separated away from the electromagnet, and the switch 214 is brought into an OFF-state. As a result, the electric connection between the coil 208, the charging circuit 90 and the battery 44 is cut off, and then the mutual inductance mi between the coil 204 and the coil 208 changes abruptly.

The mutual inductance detecting unit 200 detects electric current flowing through the coil 204. When the magnitude of the electric current changes temporally abruptly, the mutual inductance detecting unit 200 judges that the mutual inductance mi has changed abruptly due to switching of the switch 214 from an ON-state to an OFF-state.

When the mutual inductance detecting unit 200 detects an abrupt change of the mutual inductance mi, the feeding controller 86 judges that the charging controller 108 has determined stoppage (inhibition) of charging the battery 44. Then, the feeding controller 86 stops supply of electric energy (high-frequency electric power) to the LC resonator 84.

In the image capturing system 10f according to the fifth modification, even if the feeding inhibition signal is not supplied for some reasons, the power feeder 25 can stop contactless power feeding based on detection of an abrupt temporal change of the mutual inductance mi by the mutual inductance detecting unit 200, thereby performing feeding control of the battery 44 accurately and reliably. Thus, the power feeder 25 can judge, on its own, whether power feeding to the battery 44 should be inhibited or not, even without supply of the feeding inhibition signal from the charging controller 108.

In the above explanations, if it is judged that the remaining power level of the battery 44 is sufficient, then a feeding inhibition signal and an image capturing permission signal are transmitted to perform charging inhibition control arising from starting of image capturing. When the remaining power level of the battery 44 is sufficient, the following charging inhibition control may be performed instead of the above charging inhibition control. That is, a power switch (not shown) is provided on a side surface of the electronic cassette 24. A doctor 18 or a technician operates the power switch to start image-capturing, and then the image capturing permission signal and the feeding inhibition signal are transmitted to perform charging inhibition control.

With the radiographic image capturing systems 10, 10a, 10b, 10c, 10d, 10f, the electronic cassette 24 and the radiation detecting apparatus 152, 164 are movable. Even when the electronic cassette 24 and the radiation detecting apparatus 152, 164 are set in a desired image capturing position, they can easily be contactlessly supplied with electric power by the power feeder 25. Since the electronic cassette 24 and the radiation detecting apparatus 152, 164 have the end-of-A/D-conversion determining unit, the charging controller, the image capturing controller, the end-of-information-delivery determining unit and the charging intensity switching unit, the contactless (wireless) power feeding is not carried out at least until the A/D conversion of the detected radiographic image information is finished. Consequently, it is possible to capture radiographic images of high quality without being adversely affected by noise caused by the wireless power feeding, and also to quickly charge the battery 44 while no radiographic images are being captured, i.e., after the image capturing process has been finished.

Although certain preferred embodiments of the present invention have been shown and described in detail, it should be understood that various changes and modifications may be made therein without departing from the scope of the appended claims.

What is claimed is:
1. A radiation detecting apparatus comprising:
  a radiation detector for detecting radiation applied from an external image capturing apparatus and transmitted through a subject and converting the detected radiation into radiographic image information;
  a battery for activating the radiation detector;
  a determining unit for determining whether image-capturing with respect to the subject is performed or not, and/or whether delivery of the radiographic image information from the radiation detector is performed or not; and
  a charging controller for controlling charging of the battery by an external charging apparatus based on a determination result by the determining unit.

2. A radiation detecting apparatus according to claim 1, wherein when the determining unit determines that the image-capturing with respect to the subject is being performed, the charging controller inhibits the charging apparatus from charging the battery, and/or when the determining unit determines that the delivery of the radiographic image information from the radiation detector is being performed, the charging controller limits the charging of the battery by the charging apparatus.

3. A radiation detecting apparatus according to claim 2, further comprising:
  an A/D converter for performing an A/D conversion to convert the radiographic image information into digital radiographic image information; and
  an image memory for storing the digital radiographic image information,
  wherein the determining unit includes:

an end-of-A/D-conversion determining unit for determining whether the A/D conversion is finished or not; and an end-of-information-delivery determining unit for determining whether any one of transfer of the radiographic image information from the A/D converter to the image memory, storage of the radiographic image information into the image memory and output of the radiographic image information from the image memory to external equipment is finished or not, wherein when the end-of-A/D conversion determining unit determines that the A/D conversion is finished, the charging controller controls the charging apparatus to charge the battery at a first charging intensity, and wherein when the end-of-information determining unit determines that any one of the transfer of the radiographic image information from the A/D converter to the image memory, the storage of the radiographic image information into the image memory and the output of the radiographic image information from the image memory to external equipment is finished, the charging controller controls the charging apparatus to charge the battery at a second charging intensity that is higher than the first charging intensity.

4. A radiation detecting apparatus according to claim 3, further comprising a signal transmitting/receiving unit for transmitting and receiving signals to and from external equipment, wherein the charging controller generates a charging inhibition signal for inhibiting the charging apparatus from charging the battery in synchronization with application of the radiation to the subject, and the signal transmitting/receiving unit transmits the charging inhibition signal to external equipment.

5. A radiation detecting apparatus according to claim 4, further comprising a charging intensity switching unit for switching a charging intensity of the battery to the first charging intensity or the second charging intensity, wherein when the end-of-A/D-conversion determining unit determines that the A/D conversion is finished, the charging controller generates a charging permission signal for permitting the charging apparatus to charge the battery, wherein when the charging controller determines charging of the battery at the first charging intensity, the charging intensity switching unit generates a first charging control signal for controlling the charging apparatus to charge the battery at the first charging intensity, and when the charging controller determines charging of the battery at the second charging intensity, the charging intensity switching unit generates a second charging control signal for controlling the charging apparatus to charge the battery at the second charging intensity, and wherein the signal transmitting/receiving unit transmits the charging permission signal and the first charging control signal or the second charging control signal, to external equipment.

6. A radiation detecting apparatus according to claim 4, further comprising a charging intensity switching unit for switching a charging intensity of the battery to the first charging intensity or the second charging intensity, wherein when the end-of-A/D-conversion determining unit determines that the A/D conversion is finished, the charging controller generates a charging permission signal for permitting the charging apparatus to charge the battery, wherein when the charging controller determines charging of the battery at the first charging intensity, the charging intensity switching unit controls the end-of-A/D-conversion determining unit to output a determination result representing that the A/D conversion is finished, and when the charging controller determines charging of the battery at the second charging intensity, the charging intensity switching unit controls the end-of-information-delivery determining unit to output a determination result representing that any one of the transfer of the radiographic image information from the A/D converter to the image memory, the storage of the radiographic image information into the image memory and the output of the radiographic image information from the image memory to external equipment is finished, and wherein the signal transmitting/receiving unit transmits the charging permission signal and the determination result output from the end-of-A/D-conversion determining unit or the determination result output from the end-of-information-delivery determining unit, to external equipment.

7. A radiation detecting apparatus according to claim 4, wherein when the image capturing apparatus transmits an image-capturing request signal indicating that application of the radiation to the subject is started, and the signal transmitting/receiving unit receives the image-capturing request signal, the charging controller generates charging inhibition signal.

8. A radiation detecting apparatus according to claim 7, further comprising an image capturing controller for controlling application of the radiation by the image capturing apparatus, wherein when the signal transmitting/receiving unit receives the image-capturing request signal, the image capturing controller generates an image-capturing permission signal for permitting application of the radiation, and wherein the signal transmitting/receiving unit transmits the image-capturing permission signal to external equipment.

9. A radiation detecting apparatus according to claim 4, wherein the signal transmitting/receiving unit comprises a wireless transceiver for transmitting and receiving signals to and from external equipment by way of wireless communication.

10. A radiation detecting apparatus according to claim 1, wherein the charging apparatus comprises a contactless power feeder, the radiation detecting apparatus further comprising a contactless power receiving for receiving electric power supplied contactlessly by the contactless power feeder and supplying the battery with the received electric power.

11. A radiographic image capturing system comprising:

an image capturing apparatus for applying radiation to a subject;

a radiation detecting apparatus including a radiation detector for detecting the radiation transmitted through the subject and converting the detected radiation into radiographic image information, and a battery for activating the radiation detector;

a determining unit for determining whether image-capturing with respect to the subject is performed or not, and/or whether delivery of the radiographic image information from the radiation detector is performed or not;

a charging apparatus which is capable of charging the battery;

a controller for controlling the image capturing apparatus, the radiation detecting apparatus and the charging apparatus; and a charging controller for controlling charging of the battery by the charging apparatus based on a determination result by the determining unit.

12. A radiographic image capturing system according to claim 11, wherein when the determining unit determines that the image-capturing with respect to the subject is being performed, the charging controller inhibits the charging apparatus from charging the battery, and/or when the determining unit determines that the delivery of the radiographic image information from the radiation detector is being performed, the charging controller limits the charging of the battery by the charging apparatus.

13. A radiographic image capturing system according to claim 12, wherein the radiation detecting apparatus further includes:
an A/D converter for performing an A/D conversion to convert the radiographic image information into digital radiographic image information; and
an image memory for storing the digital radiographic image information,
wherein the determining unit includes:
an end-of-A/D-conversion determining unit for determining whether the A/D conversion is finished or not; and
an end-of-information-delivery determining unit determining whether any one of transfer of the radiographic image information from the A/D converter to the image memory, storage of the radiographic image information into the image memory and output of the radiographic image information from the image memory to external equipment is finished or not, and
wherein when the end-of-A/D-conversion determining unit determines that the A/D conversion is finished, the charging controller controls the charging apparatus to charge the battery at a first charging intensity, and
wherein when the end-of-information-delivery determining unit determines that any one of the transfer of the radiographic image information from the A/D converter to the image memory, the storage of the radiographic image information into the image memory and the output of the radiographic image information from the image memory to external equipment is finished, the charging controller controls the charging apparatus to charge the battery at a second charging intensity that is higher than the first charging intensity.

14. A radiographic image capturing system according to claim 13, wherein the charging controller generates a charging inhibition signal for inhibiting the charging apparatus from charging the battery in synchronization with application of the radiation to the subject.

15. A radiographic image capturing system according to claim 14, further comprising a charging intensity switching unit switching a charging intensity of the battery to the first charging intensity or the second charging intensity,
wherein when the end-of-A/D-conversion determining unit determines that the A/D conversion is finished, the charging controller generates a charging permission signal for permitting the charging apparatus to charge the battery, and
wherein when the charging controller determines charging of the battery at the first charging intensity, the charging intensity switching unit generates a first charging control signal for controlling the charging apparatus to charge the battery at the first charging intensity, and when the charging controller determines charging of the battery at the second charging intensity, the charging intensity switching unit generates a second charging control signal for controlling the charging apparatus to charge the battery at the second charging intensity.

16. A radiographic image capturing system according to claim 14, further comprising a charging intensity switching unit for switching a charging intensity of the battery to the first charging intensity or the second charging intensity,
wherein when the end-of-A/D-conversion determining unit determines that the A/D conversion is finished, the charging controller generates a charging permission signal for permitting the charging apparatus to charge the battery, and
wherein when the charging controller determines charging of the battery at the first charging intensity, the charging intensity switching unit controls the end-of-A/D-conversion determining unit to output a determination result representing that the A/D conversion is finished, and when the charging controller determines charging of the battery at the second charging intensity, the charging intensity switching unit controls the end-of-information-delivery determining unit to output a determination result representing that any one of the transfer of the radiographic image information from the A/D converter to the image memory, the storage of the radiographic image information into the image memory and the output of the radiographic image information from the image memory to external equipment is finished.

17. A radiographic image capturing system according to claim 14, wherein when the image capturing apparatus outputs an image-capturing request signal indicating that application of the radiation to the subject is started, the charging controller generates the charging inhibition signal.

18. A radiographic image capturing system according to claim 17, further comprising an image capturing controller for controlling application of the radiation by the image capturing apparatus,
wherein when the image capturing apparatus outputs the image-capturing request signal, the image capturing controller generates an image-capturing permission signal for permitting application of the radiation.

19. A radiographic image capturing system according to claim 18, wherein all of the end-of-A/D-conversion determining unit, the end-of-information-delivery determining unit, the charging controller, the charging intensity switching unit and the image capturing controller are provided in any one of the radiation detecting apparatus, the controller, the image capturing apparatus and the charging apparatus, or in each of at least two thereof, or
the end-of-A/D-conversion determining unit, the end-of-information-delivery determining unit, the charging controller, the charging intensity switching unit and the image capturing controller are provided in at least two of the radiation detecting apparatus, the controller, the image capturing apparatus and the charging apparatus.

20. A radiographic image capturing system according to claim 19, wherein a signal transmitting/receiving unit for receiving the image-capturing request signal and transmitting, to external equipment, the charging permission signal and the first charging control signal, the second charging control signal, the charging inhibition signal or the image-capturing permission signal, is further provided in the radiation detecting apparatus, the controller, the image capturing apparatus and/or the charging apparatus that have at least one of the end-of-A/D-conversion determining unit, the end-of-information-delivery determining unit, the charging controller, the charging intensity switching unit and the image capturing controller.

21. A radiographic image capturing system according to claim 20, wherein the signal transmitting/receiving unit comprises a wireless transceiver for transmitting and receiving signals to and from external equipment by way of wireless communication.

22. A radiographic image capturing system according to claim 11, wherein the charging apparatus comprises a contactless power feeder, and the radiation detecting apparatus further comprises a contactless power receiver for receiving electric power supplied contactlessly by the contactless power feeder and supplying the battery with the received electric power.

23. A method of capturing a radiographic image by applying radiation to a subject by an image capturing apparatus, detecting the radiation with a radiation detector of a radiation detecting apparatus, and converting the detected radiation into radiographic image information with the radiation detector, the method comprising the step of, when the radiation detector is activated by a battery which is capable of being charged by the charging apparatus, controlling charging of the battery by a charging apparatus based on whether image-capturing with respect to the subject is performed or not, and/or whether delivery of the radiographic image information from the radiation detector is performed or not.

* * * * *